United States Patent [19]

Tomita et al.

[11] Patent Number: 5,682,889
[45] Date of Patent: Nov. 4, 1997

[54] METHOD AND APPARATUS FOR DEDUCING BIOELECTRIC CURRENT SOURCES

[75] Inventors: Sadamu Tomita, Fushimi-ku; Shigeki Kajihara, Uji; Yoshikazu Yoshida, Tsuzuki-gun; Naokazu Yamaki, Fujisawa, all of Japan

[73] Assignee: Shimadzu Corporation, Kyoto, Japan

[21] Appl. No.: 739,461

[22] Filed: Oct. 29, 1996

Related U.S. Application Data

[62] Division of Ser. No. 252,788, Jun. 2, 1994, Pat. No. 5,601,081.

[30] Foreign Application Priority Data

| Jun. 4, 1993 | [JP] | Japan | 5-160450 |
|---|---|---|---|
| Jun. 4, 1993 | [JP] | Japan | 5-160451 |
| Sep. 30, 1993 | [JP] | Japan | 5-245615 |
| Nov. 26, 1993 | [JP] | Japan | 5-320956 |
| Nov. 26, 1993 | [JP] | Japan | 5-320958 |
| Mar. 17, 1994 | [JP] | Japan | 6-47220 |

[51] Int. Cl.$^6$ ............................................. A61B 5/05
[52] U.S. Cl. ................... 128/653.1; 324/244; 324/248; 324/260; 128/731
[58] Field of Search ......................... 128/653.1, 731; 324/244, 248, 260

[56] References Cited

U.S. PATENT DOCUMENTS

| 5,170,119 | 12/1992 | Sekihara et al. | 128/653.1 |
|---|---|---|---|
| 5,206,589 | 4/1993 | Kado et al. | 128/653.1 |
| 5,263,487 | 11/1993 | Sakamoto et al. | 128/732 |
| 5,269,325 | 12/1993 | Robinson et al. | 128/653.1 |
| 5,426,365 | 6/1995 | Sekihara et al. | 128/653.1 |

FOREIGN PATENT DOCUMENTS

| 0527482A1 | 2/1993 | European Pat. Off. | |
|---|---|---|---|
| 4126949 | 2/1993 | Germany | 128/653.1 |
| 4218563A1 | 2/1993 | Germany | |
| 4226413A1 | 2/1993 | Germany | |
| 5220124 | 8/1993 | Japan | 128/653.1 |

OTHER PUBLICATIONS

1256 IEEE Engineering in Medicine & Biology, Society 11th Annual International Conference, "New Approaches to Source Localization in Meg," Christopher W. Crowley, et al, Biomagnetic Technologies, Inc., San Diego, CA. Nov. 1989.
8088 IEEE Transactions on Biomedical Engineering, 39 (1992) Jun., No. 6, New York, US, "Maximum–Likelihood Estimation of Current–Dipole Parameters for Data Obtained Using Multichannel Magnetometer".
8078 Proceedings of the IEEE, 78 (1990), Jun. No. 6, New York, US, pp. 973–989, "A Review of Magnetic Sensors," James E. Lenz.

*Primary Examiner*—Brian L. Casler
*Attorney, Agent, or Firm*—Nikaido, Marmelstein, Murray & Oram LLP

[57] ABSTRACT

A method and apparatus for deducing physical quantities such as positions, sizes and orientations of bioelectric current sources. Minute magnetic fields formed by the bioelectric current sources in a region under examination of an examinee are measured with a plurality of magnetic sensors arranged adjacent the region under examination. A plurality of lattice points are set in the region under examination. Physical quantities of the current sources are derived by solving a relational expression of unknown current sources at the lattice points and field data provided by the magnetic sensors, with a condition added thereto to minimize a norm of a vector having the current source at each of the lattice points. The lattice points are moved toward a lattice point having a large current value among the current sources computed. Checking is made whether a minimum distance among the lattice points having been moved is below a predetermined value. The current source computing step to the checking step are repeated for the lattice points having been removed, when the minimum distance exceeds the predetermined value, and the current source corresponding to a magnetic field occurring when the minimum distance is determined to be below the predetermined value is identified to be a true current source.

2 Claims, 26 Drawing Sheets

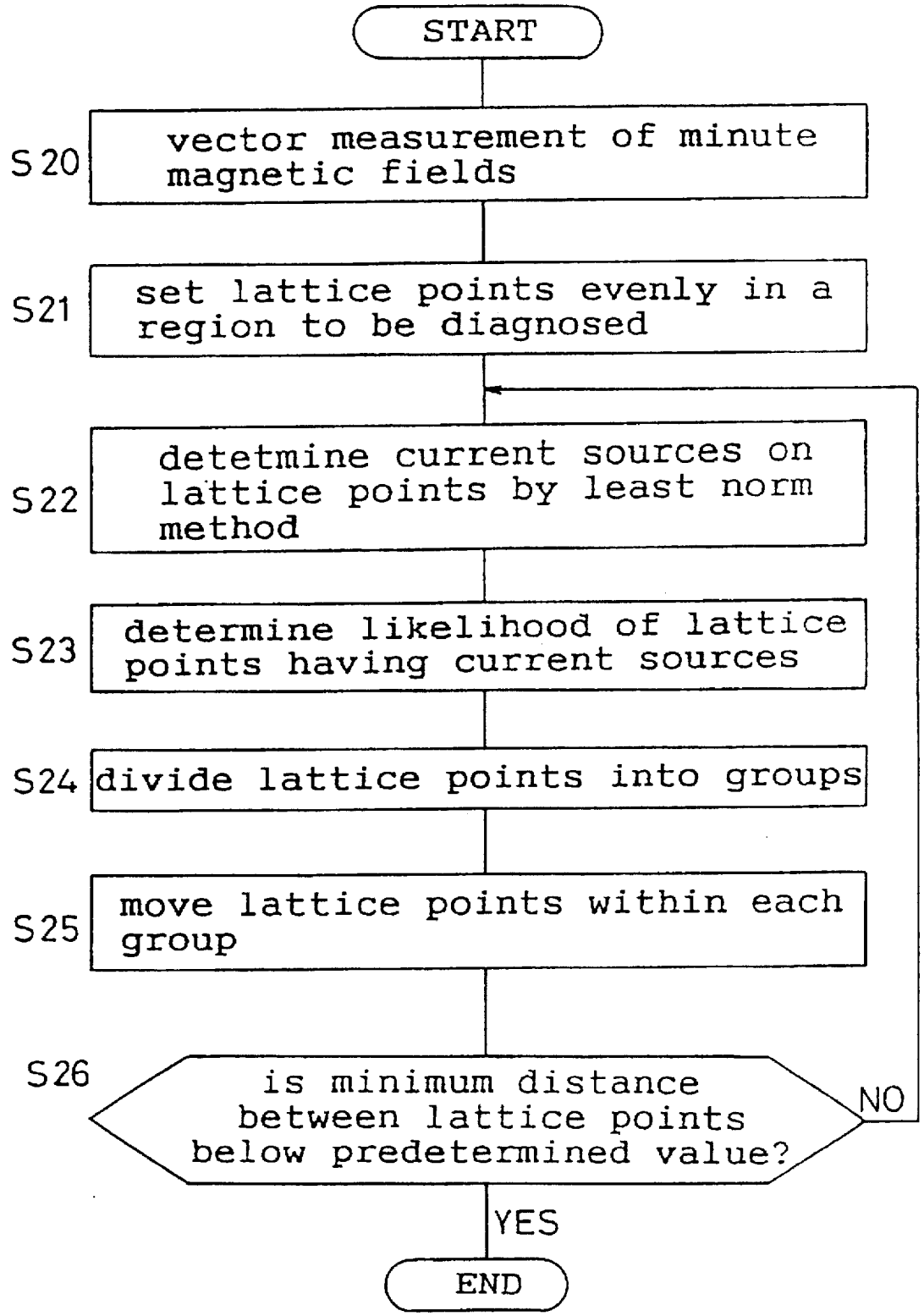

vector measurement radial measurement

α = 0.3

α = 0.5

α = 0.3

α = 0.5 f = 4.119901e-06 f = 3.926445e-07

METHOD AND APPARATUS FOR DEDUCING BIOELECTRIC CURRENT SOURCES

This is a division of application Ser. No. 08/252,788 filed Jun. 2, 1994 U.S. Pat. No. 5,601,081.

BACKGROUND OF THE INVENTION

(1) Field of the Invention

This invention relates to a method and apparatus for deducing positions, orientations and sizes of bioelectric current sources.

(2) Description of the Related Art

A stimulus given to a living body breaks polarization across cell membranes and generates bioelectric currents. Such bioelectric currents take place in the brain and the heart, and are recorded as an electro-oencephalogram or an electrocardiogram. The magnetic fields formed by such bioelectric currents are recorded as a magnetoencephalogram or a magnetocardiogram.

In recent years, a senor using a SQUID (Super-conducting Quantum Interface Device) has been developed as a device for measuring minute magnetic fields in the living body. This sensor may be placed outside the head to measure, in a painless and harmless way, minute magnetic fields formed by current dipoles (hereinafter simply called current sources also) which are bioelectric current sources occurring in the brain. The positions, orientations and sizes of the current sources relating to a lesion are deduced from the magnetic field data thus gained. The current sources deduced are superposed on sectional images obtained from a radiographic CT apparatus or MRI apparatus, to determine a physical position and other features of a disease or the like.

One example of conventional methods for deducing current sources uses a least norm method (see, for example, W. H. Kullmann, K. D. Jandt, K. Rehm, H. A. Schlitte, W. J. Dallas and W. E. Smith, Advances in Biomagnetism, pp. 571–574, Plenum Press, New York, 1989).

The conventional method of deducing current sources using the least norm method will be described hereinafter with reference to FIG. 1.

As shown in FIG. 1, a multichannel SQUID sensor 1 is disposed adjacent an examinee M. The multichannel SQUID sensor 1 has a multiplicity of magnetic sensors (pickup coils) S1 to Sm immersed in a coolant such as liquid nitrogen within a vessel called a Dewar.

On the other hand, a multiplicity of lattice points "1" to "n" are set in a region to be diagnosed, e.g. the brain, of the examinee M. Unknown current sources (current dipoles) are assumed for the respective lattice points, which are expressed by three-dimensional vectors VPj (j=1 to n). Then, the respective magnetic sensors S1 to Sm of the SQUID sensor 1 detect magnetic fields B1 to Bm which are expressed by the following equations (1):

$$B1 = \sum_{j=1}^{n} (VPj \cdot \alpha 1j)$$
$$B2 = \sum_{j=1}^{n} (VPj \cdot \alpha 2j)$$
$$\vdots$$
$$Bm = \sum_{j=1}^{n} (VPj \cdot \alpha mj) \quad (1)$$

In the equations (1), $VPj=(Pjx, Pjy, Pjz)$, and $\alpha ij=(\alpha ijx, \alpha ijy, \alpha ijz)$. $\alpha ij$ is a known coefficient representing intensity of a magnetic field detected in the position of each magnetic sensor S1 to Sm, where the current sources of unit sizes in X, Y and Z directions are arranged on the lattice points.

If $[B]=(B1, B2, \ldots Bm)$, and $[P]=(P1x, P1y, P1z, P2x, P2y, P2z, \ldots Pnx, Pny, Pnz)$, then the equations (1) are rewritten as the following linear relationship (2):

$$[B]=A[P] \quad (2)$$

In the equation (2), A is a matrix having 3n×m elements expressed by the following equation (3):

$$A = \begin{pmatrix} \alpha 11X, \alpha 11Y, \alpha 11Z & \ldots & \alpha 1nX, \alpha 1nY, \alpha 1nZ \\ \cdot & & \cdot \\ \cdot & & \cdot \\ \cdot & & \cdot \\ \alpha m1X, \alpha m1Y, \alpha m1Z & \ldots & \alpha mnX, \alpha mnY, \alpha mnZ \end{pmatrix} \quad (3)$$

If the inverse matrix of A is expressed by $A^-$, [P] is expressed by the following equation (4):

$$[P]=A^-[B] \quad (4)$$

The least norm method is based on the premise that the number of unknowns 3n (where the sizes in X, Y and Z directions of the current sources assumed for the respective lattice points are taken into account) is greater than the number of equations m (the number of magnetic sensors S1 to Sm). This method finds solutions for current sources [P] by applying the condition that norm ||[P]|| of current sources [P] is minimized. The solutions could be obtained uniformly by equalizing the number of equations m and the number of unknowns 3n, but such solutions would be very unstable. For this reason, the least norm method is employed.

By applying the condition that norm ||[P]|| of current sources [P] is minimized, the above equation (4) is rewritten as the following equation (5):

$$[P]=A^{30}[B] \quad (5)$$

where $A^+$ is a general inverse matrix expressed by the following equation (6):

$$A^+=A'(AA')^{-1} \quad (6)$$

where $A'$ is a transposed matrix of A.

The orientatins and sizes of the current sources VPj on the respective lattice points are deduced by solving the above equation (5). The current source having the greatest value thereamong is regarded as the closest to a true current source. This is the principle of the current source deducing method based on the least norm method.

In order to improve the position resolving power of the least norm method, proposals have been made to gain least norm solutions repeatedly while subdividing the lattice points (see, for example, Y. Okada, J. Huang and C. Xu, 8th International Conference on Bio-magnetism, Munster, August 1991). This method will be described briefly with reference to FIG. 2.

FIG. 2 is an enlarged view of part of the lattice points N shown in FIG. 1. Reference J in FIG. 2 denotes the lattice point having the current source deduced by the above least norm method as being close to the true current source. A group of subdivided lattice points M (shown in small black spots in FIG. 2) is additionally established around this lattice point J. The technique described above is applied to the newly established group of lattice points M as included in the initially established group of lattice points N, to deduce a current source still closer to the true current source.

The prior art described above has the following disadvantage.

The conventional method illustrated in FIG. 2 involves an increased number of lattice points since the subdivided lattice points M are newly established in addition to the initially established lattice points N. Consequently, vector [P] in equation (5) has a large number of elements which lowers the precision in computing the least norm solutions.

SUMMARY OF THE INVENTION

This invention has been made having regard to the state of the art noted above, and its primary object is to provide a method and apparatus for deducing bioelectric current sources with high precision.

The above object is fulfilled, according to this invention, by a method of deducing physical quantities such as positions, sizes and orientations of bioelectric current sources, comprising:

- a magnetic field meazuring step for measuring minute magnetic fields formed by the bioelectric current sources in a region under examination of an examinee, with a plurality of magnetic sensors arranged adjacent the region under examination;
- a lattice point setting step for setting a plurality of lattice points in the region under examination;
- a current source computing step for deriving physical quantities of the current sources by solving a relational expression of unknown current sources at the lattice points and field data provided by the magnetic sensors, with a condition added thereto to minimize a norm of a vector having the current source at each of the lattice points;
- a lattice point rearranging step for moving the lattice points toward a lattice point having a large current value among the current sources computed;
- a checking step for checking whether a minimum distance among the lattice points having been moved is below a predetermined value; and
- a current source identifying step for repeating the current source computing step to the checking step for the lattice points having been removed, when the minimum distance exceeds the predetermined value, and regarding as a true current source the current source corresponding to a magnetic field occurring when the minimum distance is determined to be below the predetermined value at the checking step.

This invention has the following functions.

The lattice point having a large current value among the current sources computed at the current source computing step is not a true current source but a current source close to the true current source. Thus, at the lattice point rearranging step, the other lattice points set at the lattice point setting step are moved toward the lattice point having a large current value. Current sources are deduced similarly for the rearranged lattice points. That is, according to this invention, a true current source is deduced by moving the lattice points without varying the number of lattice points. Consequently, a true current source is deduced with precision while maintaining the computing precision of the least norm method.

Where a plurality of true current sources (current sources having a large value) exist, the above method poses a question which lattice point should be selected as one toward which the other are to be moved. It is preferred, in such a case, that likelihood of current sources being present at the lattice points is derived from the physical quantities of the current sources at the lattice points deduced, and the lattice points are divided into a plurality of groups based on the likelihood derived. Then, current sources may be deduced with precision even where a plurality of true current sources are present.

In the above technique, the physical quantities of the current sources for determining likelihood of current sources being present at the respective lattice points are, for example, the size of the current source at each lattice point and density of lattice points around that lattice point. It is then necessary to determine empirically a parameter representing the degree of influence of the lattice point density on the likelihood of current sources. However, this parameter setting is not necessarily easy, and an improper value selected will lower the current source deducing precision.

To obviate such parameter setting, it is preferable to measure simultaneously three orthogonal components (vector measurement) of the minute magnetic fields formed by the bioelectric current sources in the region under examination, and to deduce current sources based on measured field data of the three orthogonal components. With such vector measurement, the measured field data have a high degree of mutual independence, resulting in improved spatial resolving power. Since this eliminates the need to consider lattice point density around each lattice point as a factor applied to the likelihood of a current source being present at each lattice point, the above parameter setting is made unnecessary.

For example, a group function showing the influence of a current source at a certain lattice point on the other lattice points is used in dividing the lattice points into a plurality of groups based on the likelihood of current sources being present at the lattice points. It is then necessary to determine empirically a parameter (moving parameter) determining a form of the group function. However, this parameter setting is not necessarily easy either, and an improper value selected will lower the current source deducing precision. Preferably, this moving parameter is automatically optimized with a condition to minimize a norm of a solution (a vector having the current source at each lattice point as an element).

The deducing method using the least norm method described above is based on the premise that the number of unknowns 3n (n being the number of lattice points), where the sizes in X, Y and Z directions of the current sources assumed for the respective lattice points are taken into account, is greater than the number of magnetic sensors m (the number of equations), i.e. $3n > m$. Consequently, the coefficient matrix representing the relationship between the unknown current sources at the lattice points and measured magnetic fields could be lowered in level to render the solutions unstable. Further, at the step of identifying an optimal current source, whether a minimum distance between lattice points is below a predetermined value (convergent criterion) is used as a determination condition. Thus, deduction results could vary with the predetermined criterion. This problem is solved by a method according to a further aspect of this invention.

Thus, this invention provides a method of deducing physical quantities such as positions, sizes and orientations of bioelectric current sources, comprising:

a magnetic field measuring step for measuring minute magnetic fields formed by the bioelectric current sources in a region under examination of an examinee, with a plurality of magnetic sensors arranged adjacent the region under examination;

a lattice point setting step for setting a plurality of lattice points in the region under examination, the lattice points being smaller in number than the magnetic sensors;

a first current source computing step for deriving unknown current sources by adding a condition to minimize a square error of a magnetic field formed by an unknown current source at each of the lattice points and a magnetic field measured by each of the magnetic sensors;

a checking step for checking whether the square error of the magnetic field computed from the current source derived and the magnetic field actual measured by each of the magnetic sensors is a global minimum;

a lattice point rearranging step for moving the lattice points toward a lattice point having a large current value among the current sources computed at the first current source computing step, when the square error is determined to differ from the global minimum;

a current source identifying step for repeating the first current source computing step to the lattice point rearranging step, and regarding as a true current source the current source corresponding to a magnetic field occurring when the square error is determined to be a global minimum at the checking step.

According to this method, the number of magnetic sensors is larger than the number of unknowns for the lattice points set, to obtain stable solutions (current sources). The current sources may be deduced with increased precision by adopting the condition to minimize a square error of a magnetic field formed by an unknown current source at each of the lattice points and a magnetic field actually measured. Further, since the current source occurring when the square error is determined to be a global minimum is regarded as a true current source, the convergent determination value need not be set at the step of deducing a final current source. Thus, the final current source deduction may be effected uniformly.

When the above group function is used in rearranging the lattice points at the above lattice point rearranging step, a troublesome operation is involved such as for setting parameters. Further, since the lattice points is moved little by little within each group, a considerable time is consumed before results of the deduction are produced. To overcome such disadvantages, it is preferred that current sources at the lattice points are newly derived, when the square error is determined to differ from the global minimum at the checking step, by adding a condition to minimize a sum of the square error and a weighted sum of squares of the current source, and the lattice points are moved toward a lattice point having a large current value among the current sources. This technique employs the square error combined with a penalty term which is a weighted sum of squares of the current source as an evaluation function for moving the lattice points. Consequently, stable solutions are obtained even where the lattice points are not in the true current source. This allows the lattice points to be moved at a time to the vicinity of the greatest current source, thereby to shorten the time consumed in deducing the current sources. The lattice points are rearranged without using a group function, which dispenses with an operation to set parameters.

In the above technique of determining current sources at the respective lattice points by the linear least squares method, if noise mixes into the magnetic fields measured, noise components may also be calculated as solutions (current sources). This results in the disadvantage that the position of each current source deduced tends to vary. To overcome this disadvantage, it is preferred that the first current source computing step is executed to derive current sources at the lattice points by adding a condition to minimize a sum of the square error of the magnetic field formed by the unknown current source at each lattice point and the magnetic field actually measured, and a weighted sum of squares of the current source, the checking step is executed to check whether the sum of the square error and the weighted sum of squares of the current source computed is a global minimum, and when the sum is determined to differ from the global minimum, the lattice points are moved toward a lattice point having a large current value among the current sources computed. At the checking step for deducing an optimal current source, this technique evaluates the function having a weighted sum of squares of the current source (penalty term) added to the square error. The penalty term has the smaller value, the closer the current sources lie to one another. Consequently, noise components occurring discretely have little chance of being adopted as solutions.

The influence of noise components is avoided by evaluating, at the checking step for deducing an optimal current source, the function having a weighted sum of squares of the current source (penalty term) added to the square error, as noted above. However, the current sources at the lattice points deduced tend to consolidate. This results in the disadvantage that, where current sources are distributed over a certain range, a true current source could be difficult to deduce correctly. In such a case, for the condition added at the first current source computing step, i.e. the condition to minimize a sum of the square error and a weighted sum of squares of the current source, a weight for the current source is set to have the smaller value the smaller a distance is between the lattice points. At the checking step, the penalty term is excluded to check whether the square error between the magnetic fields formed by the current sources obtained at the first current source computing step and the magnetic fields actually measured is a global minimum or not. If the square error is found not to be a global minimum, the lattice points are moved toward a lattice point having a large current value among the current sources computed. According to this technique, when the lattice points concentrate locally, the influence of the penalty term diminishes. Further, since the penalty term is excluded from the criterion for identifying optimal current sources, the current sources deduced are not unnecessarily concentrated. Thus, current sources distributed over a certain range may be deduced correctly.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

FIG. 13 is a flowchart of current source deduction processing in a third embodiment;

DETAILED DESCRIPTION OF THE PREFERRED EMBODIMENTS

Preferred embodiments of this invention will be described hereinafter with reference to the drawings.

First Embodiment

An outline of an apparatus embodying this invention for deducing bioelectric current sources will be described with reference to FIG. 3.

Figure 3:
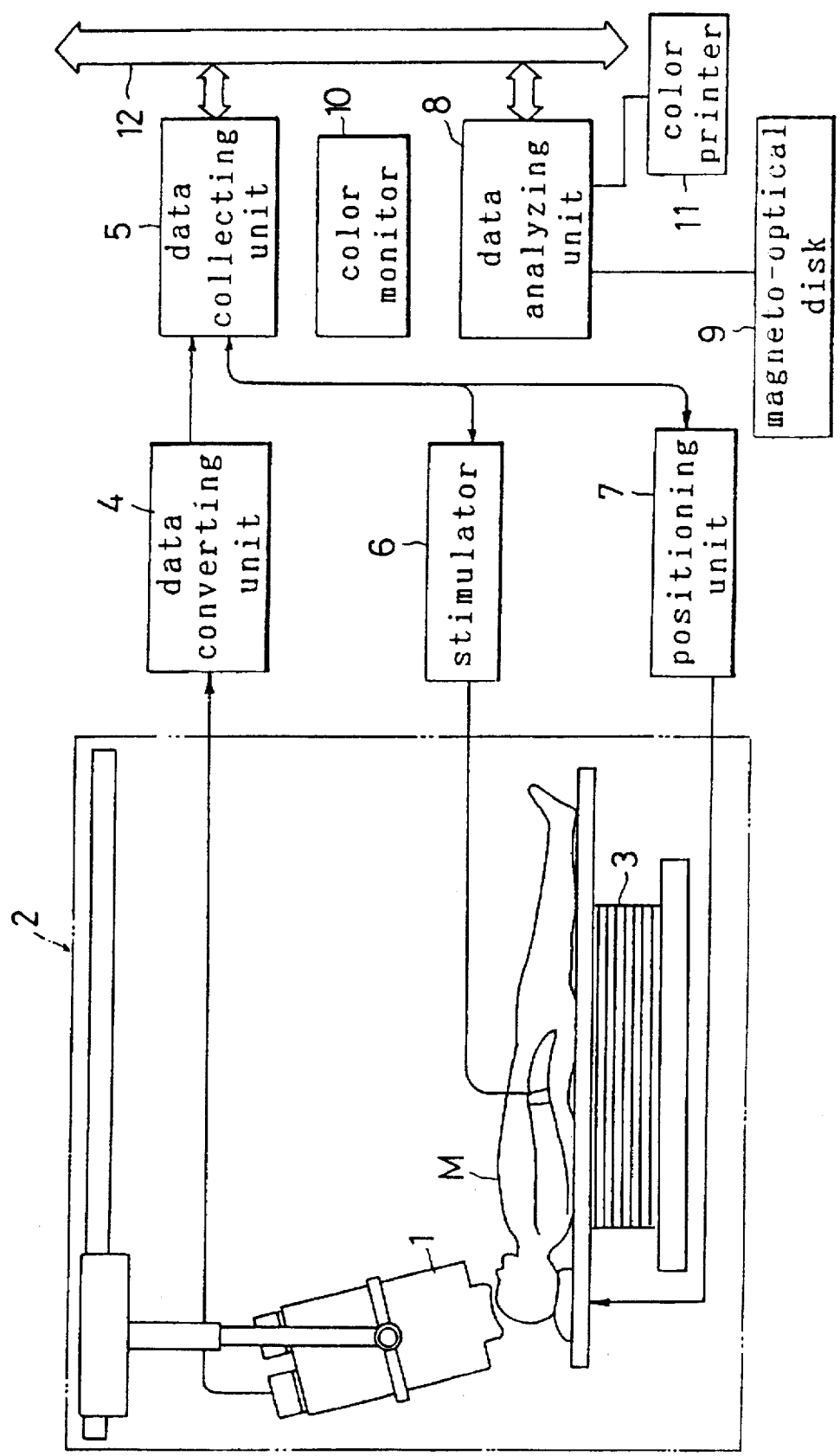
FIG. 3 is a block diagram showing an outline of an apparatus embodying the present invention.

Numeral 2 in FIG. 3 denotes a magnetic shield room. The magnetic shield room encloses a bed 3 for supporting an examinee M lying thereon, and a multi-channel SQUID sensor 1 disposed adjacent the brain of the examinee M, for example, for measuring, in a painless and harmless way, minute magnetic fields formed by bioelectric current sources occurring in the brain. As noted hereinbefore, the multichannel SQUID sensor 1 has a multiplicity of magnetic sensors immersed in a coolant within a Dewar. In this embodiment, each magnetic sensor consists of a pair of coils for detecting a magnetic field component in a radial direction, with the brain being regarded as a spherical body.

Field data detected by the multichannel SQUID sensor 1 are applied to a data converting unit 4 for conversion to digital data to be stored in a data collecting unit 5. A stimulator 6 applies electric (acoustic, optical or other) stimulation to the examinee M. A positioning unit 7 determines a positional relationship of the examinee to a three-dimensional coordinate system based on the multichannel SQUID sensor 1. For example, small coils are attached to a plurality of sites on the examinee M, and the positioning unit 7 supplies power to these small coils. Then, the coils generate magnetic fields to be detected by the multichannel SQUID sensor 1, thereby enabling determination of the position of the examinee M relative to the multichannel SQUID sensor 1. Other methods may be used to determine the position of the examinee M relative to the SQUID sensor 1. For example, a projector may be attached to the Dewar to emit a light beam to the examinee M to determine the positional relationship. Various other methods are available as disclosed in Japanese Patent Publications (Unexamined) No. 5-237065 and No. 6-788925.

A data analyzing unit 8 is used to deduce current sources in a region to be diagnosed of the examinee M, from the field data stored in the data collecting unit 5. A magneto-optical disk 9 associated with the data analyzing unit 8 stores sectional images obtained from a radiographic CT apparatus or MRI apparatus, for example. The current sources deduced by the data analyzing unit 8 may be superposed on these sectional images for display on a color monitor 10 or for printing by a color printer 11. The sectional images obtained from the radiographic CT apparatus or MRI apparatus may be transmitted directly to the data analyzing unit 8 through a communication line 12 shown in FIG. 3.

Figure 4:
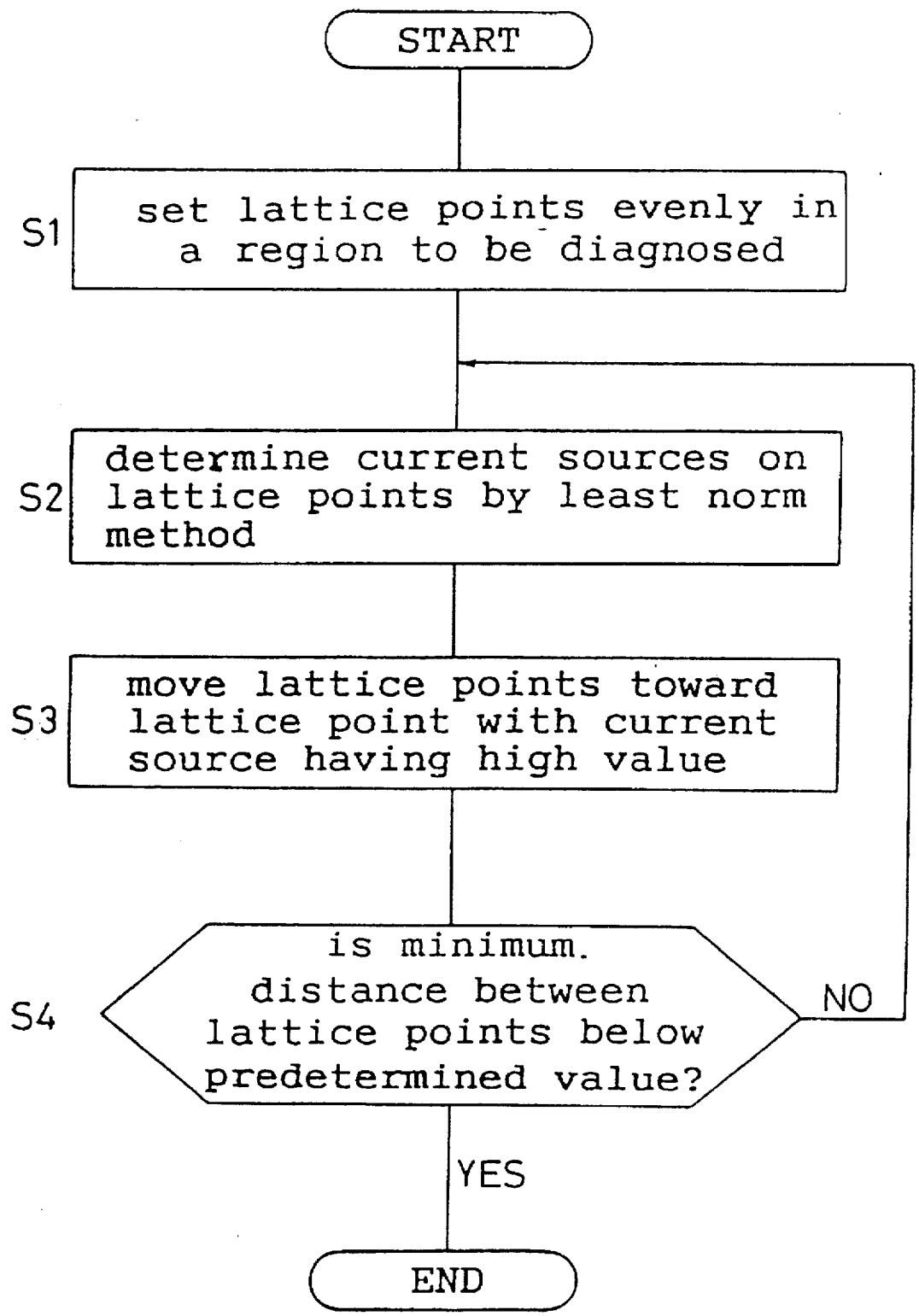
FIG. 4 is a flowchart of current source deduction processing in a first embodiment.

A sequence of current source deduction executed by the data analyzing unit 8 will be described hereinafter with reference to the flowchart shown in FIG. 4.

Figure 1:
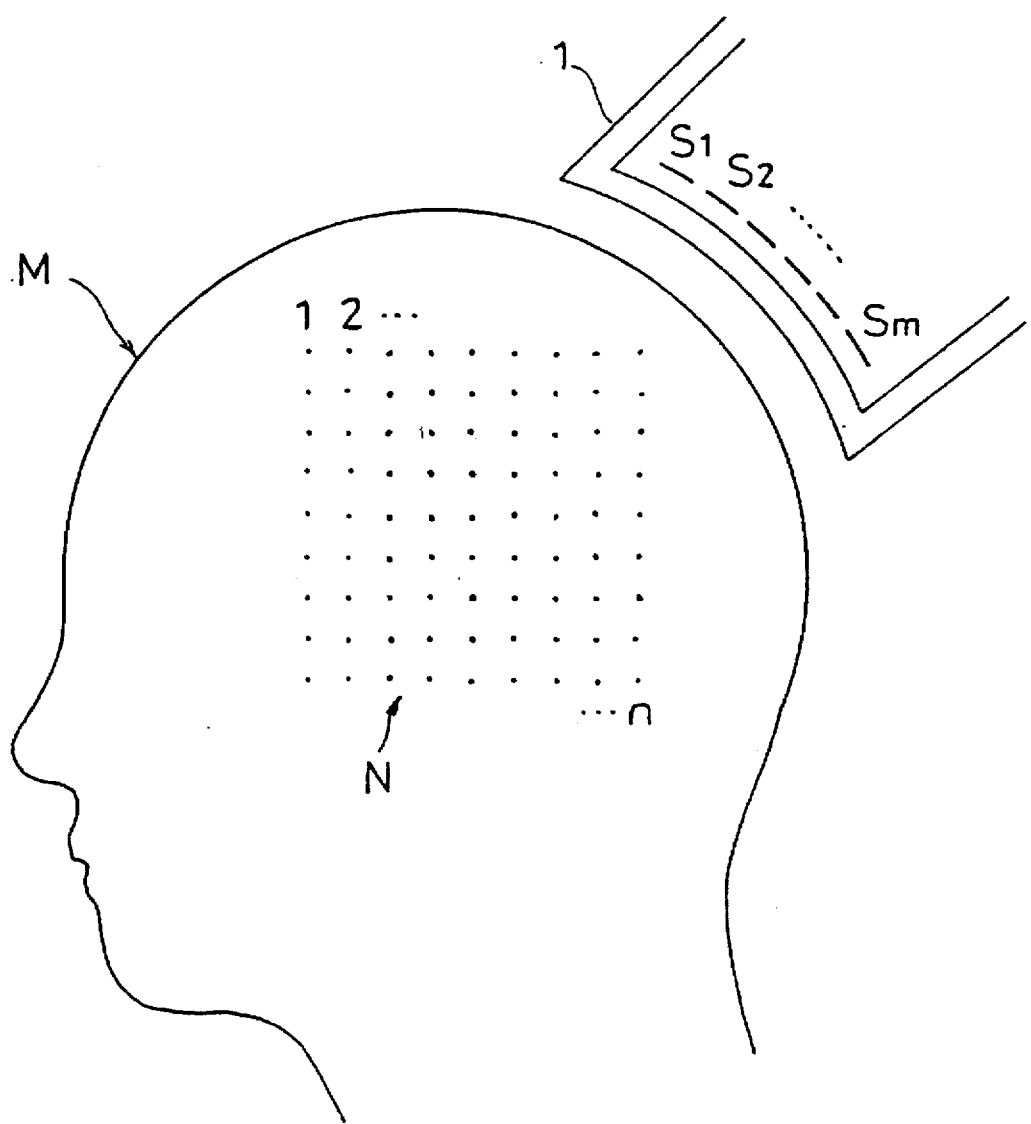
FIG. 1 is an explanatory view of a conventional method of deducing bioelectric current sources, using the least norm method.
Figure 2:
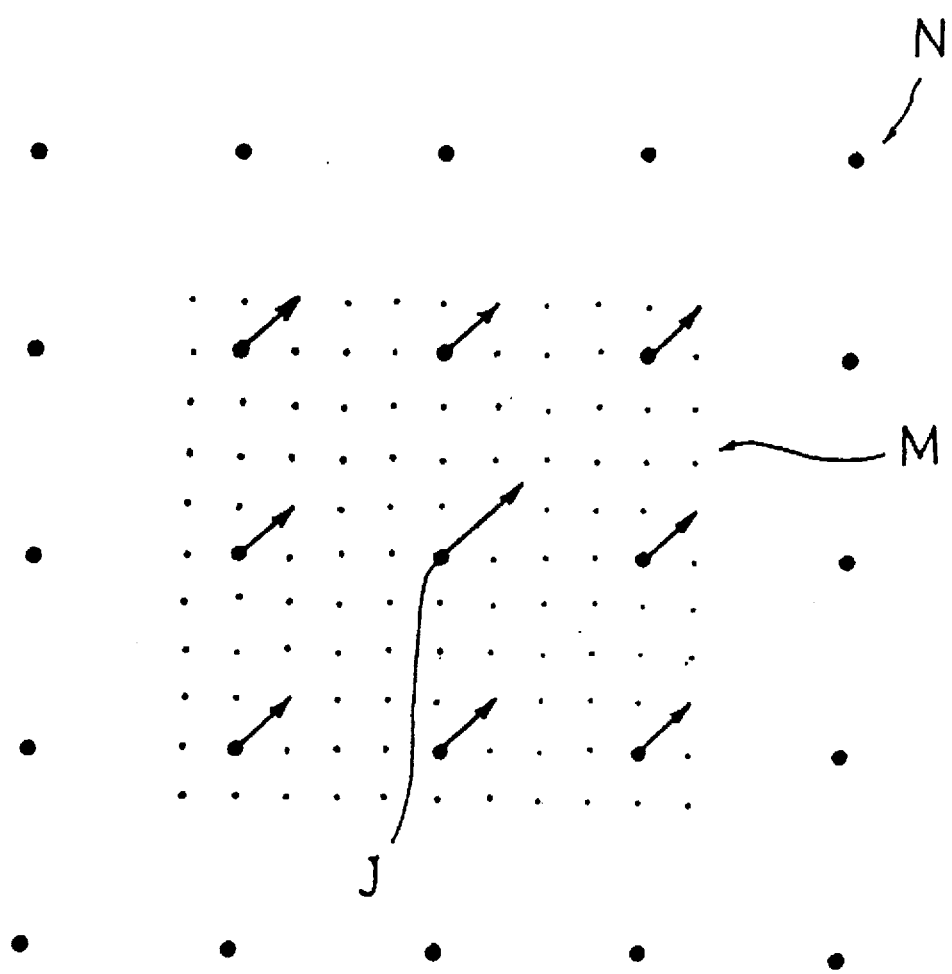
FIG. 2 is an explanatory view of another conventional method of deducing current sources.

As noted above, a positional relationship of the examinee M to the three-dimensional coordinate system based on the multichannel SQUID sensor 1 is measured and stored first. Then, as in the prior art illustrated in FIG. 1, three-dimensional lattice points N are set evenly in a region to be diagnosed, e.g. the brain, of the examinee M (step S1).

The respective coefficients in the matrix A expressed by equation (3) are computed by Biot-Savart's law (the coefficients in matrix A being computed each time the lattice points are moved as described later). Subsequently, a current source (least norm solution) at each lattice point is determined by the least norm method (step S2).

Figure 5:
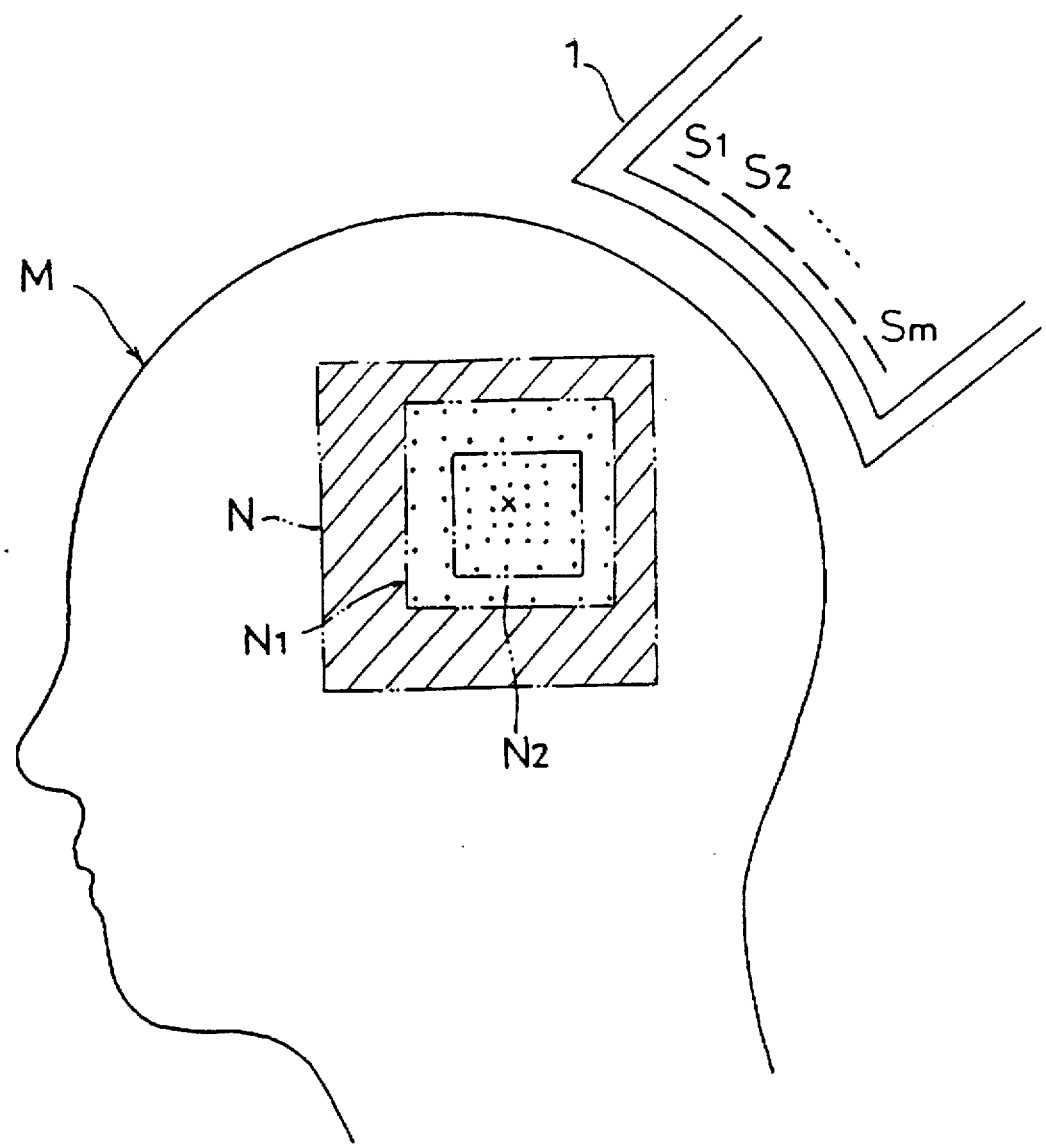
FIG. 5 is an explanatory view of lattice point movement in the first embodiment.

Next, the lattice points are moved toward a lattice point having a current source of large value among the current sources determined at step S2 (step S3). FIG. 5 shows how this step is taken. Reference N in FIG. 5 denotes the group of lattice points initially set at step S1. The lattice point marked "x" is the lattice point having a current source of large value among the current sources determined at step S2. The other lattice points are moved toward this lattice point, to form a group of lattice points N1 corresponding in number to the group of lattice points N but lying closer together.

Step S3 of moving the other lattice points toward the lattice point having a current source of large value may be executed by any suitable method, and the following is one example. Assume that, by regarding the size of the current source at each lattice point determined at step S2 as a mass, and attractive forces due to gravity act among the lattice points. Then, each lattice point moves toward a lattice point of greater mass. The lattice points are collected with the higher density, the closer they are to a lattice point having a large mass. The moving distance of each lattice point is set as appropriate.

Step S4 is executed to check whether a minimum distance between lattice points in the group of lattice points N1 formed after the movement made at step S4 is less than a predetermined distance. This distance is determined as appropriate, based on the precision of deduced positions of the current sources.

If the minimum distance between lattice points exceeds the predetermined value, the operation returns to step S2 to determine, by the least norm method, the current source of each lattice point in the group of the lattice points N1 formed by moving the original lattice points. As noted above, the number of lattice points N1 is the same as the number of original lattice points N. In the linear equation (5) (set out hereunder again) used in the least norm method,

[P]=A⁺[B]  (5)

the number of elements in vector [P] is not increased but is fixed. This means that the computing precision of the least norm solutions is maintained. On the other hand, since the lattice points have been moved, the least norm method executed a second time disregards presence of current sources in hatched regions in FIG. 5. However, these regions are, after all, separate from a position expected to include a true current source. The lattice points in these regions have hardly any chance of including the true current source. Thus, there is no fear of lowering the precision of deduction by excluding these regions.

As before, a current source at each of the lattice points N1 is determined by the least norm method (step S2). It is presumed that a current source of large value is close to the true current source. Toward the lattice point having this current source, the other lattice points are moved to form a new group of lattice points N2 (step S3).

When, after repeating the above process, a minimum distance between lattice points is found to be below the predetermined value at step S4, the current sources of the group of lattice points determined at step S2 executed the last time are regarded as corresponding to the true current source.

According to this embodiment, as understood from the foregoing description, the other lattice points are moved toward the lattice point having a current source of large value deduced by the least norm method executed first. Current sources are deduced by the least norm method executed next, with the number of lattice points remaining unchanged from the previous time, and with only the distances between the lattice points diminished. Thus, the current sources may be deduced with high precision while maintaining the precision in computing the least norm solutions.

Second Embodiment

Where a plurality of true current sources are present, the first embodiment poses a question which lattice point should be selected as one toward which the other are to be moved. The second embodiment determines likelihood of a current source being present at each lattice point from deduced physical quantities of the current source. Based on the likelihood, the lattice points are divided into a plurality of groups. For each group the lattice points are moved toward the lattice point having the greatest current source.

Figure 6:
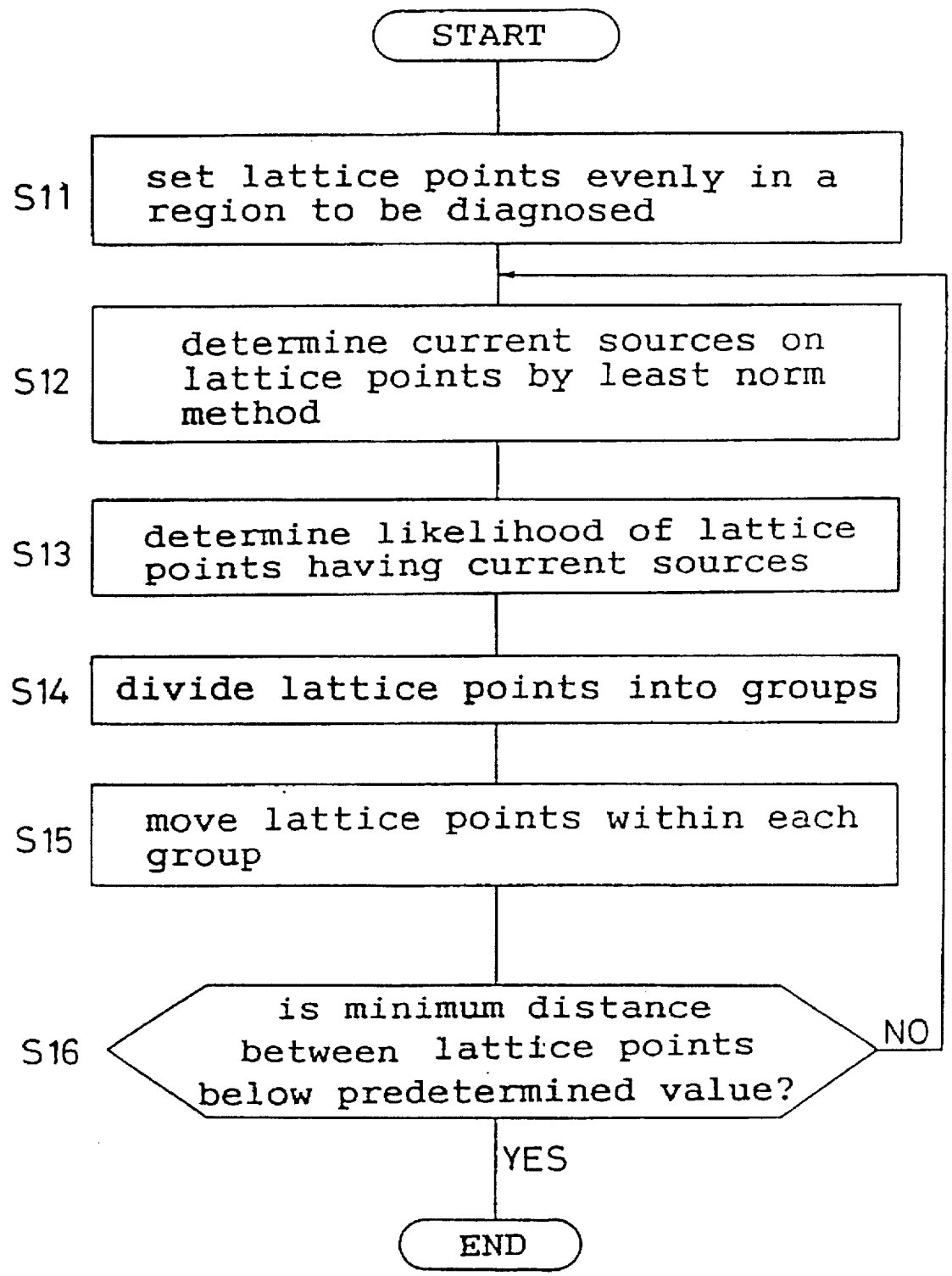
FIG. 6 is a flowchart of current source deduction processing in a second embodiment.

The outline of the apparatus and the multichannel SQUID sensor 1 in this embodiment are the same as in the first embodiment, and will not be described again. A sequence of current source deduction will be described hereinafter with reference to the flowchart shown in FIG. 6.

As in the first embodiment, three-dimensional lattice points N are set evenly in a region to be diagnosed, e.g. the brain, of the examinee M (step S11).

Then, a current source (least norm solution) at each lattice point is determined by the least norm method (step S12).

Next, where the position of the "j"th lattice point is regarded as vector Vrj, the deduced current source thereof as vector VPj, the position of the "k"th (k≠j) lattice point as vector Vrk, and the deduced current source thereof as vector VPk, likelihood Q of a current source being present at the "j"th lattice point is expressed by the following equation (7), for example. This equation is used to determine the likelihood of presence at each lattice point of the current source obtained at step S12 (step S13).

$$Q(Vrj) = |VPj| + \gamma \sum_{k=1, k\neq j}^{n} e^{-\beta|Vrk-Vrj|} \quad (7)$$

In equation (7), β is a parameter for adjusting the degree of likelihood relative to distances between the lattice points, and γ is a parameter for determining a weight of the second term. These parameters are selected empirically. Further, in the above equation, "e" is the base of natural logarithm (e=2.71828 . . . ), and "n" is a total number of lattice points.

The first term in equation (7) indicates that the greater the size of the current source at the "j"th lattice point, the greater the likelihood of the current source being present at this lattice point. The second term indicates that the higher the density of lattice points around the "j"th lattice point, the greater the likelihood of the current source being present.

In the subsequent processing, lattice points having less likelihood are moved toward lattice points of greater likelihood, to deduce current sources from a more appropriate arrangement of lattice points. To effect such movement of the lattice points, the lattice points N are divided into groups by using group function $\phi j$ expressed by the following equation (8), for example (step S14):

$$\phi j(Vrj) = Q(Vrj) \frac{1}{\sqrt{2\pi}\ \alpha} e^{\frac{|Vri-Vrj|^2}{2\alpha^2}} \quad (8)$$

Group function $\phi j$ indicates influences of the current source at the "j"th lattice point on the other lattice points. Vr in equation (8) is a position vector of a given point. $\alpha$ is an empirically selected parameter for determining a form of the functions in equation (8).

Figure 7:
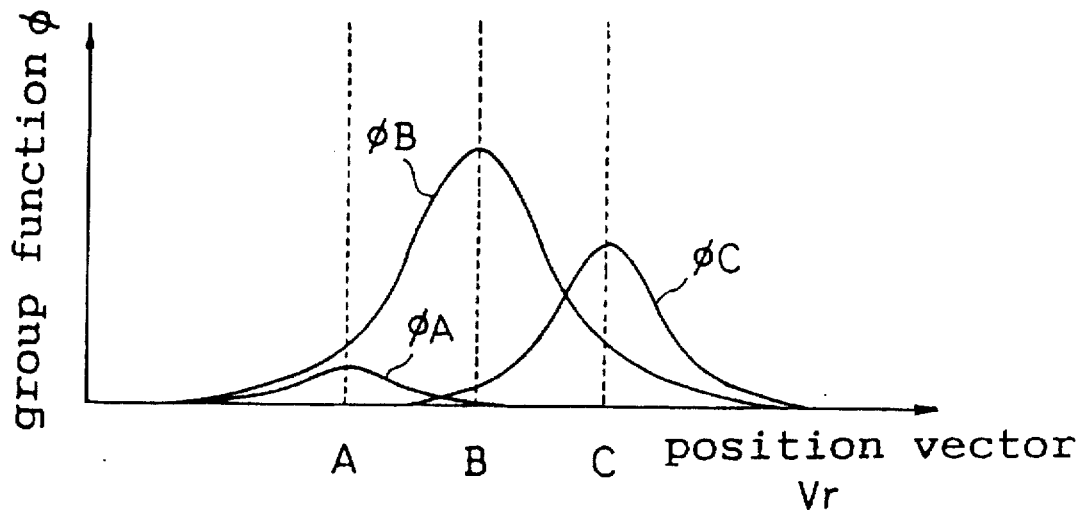
FIG. 7 is an explanatory view of group functions.

A method of dividing the lattice points N into groups by using group function $\phi j$ will be described with reference to FIG. 7. In the graph shown in FIG. 7, the vertical axis represents group function $\phi j$, and the horizontal axis a given position vector Vr. References A, B and C on the horizontal axis denote lattice points in the group of lattice points N. References $\phi A$, $\phi B$ and $\phi C$ are group functions $\phi j$ of lattice points A, B and C, respectively. In the example shown in FIG. 7, the lattice point that gives the greatest function value at lattice point A is B. In this case, therefore, lattice point A belongs to the same group as lattice point B. On the other hand, the greatest function value at lattice point C is given by lattice point C itself. Thus, lattice point C belongs to a different group to lattice points A and B. In this way, the lattice points N are divided into a plurality of groups.

Figure 8:
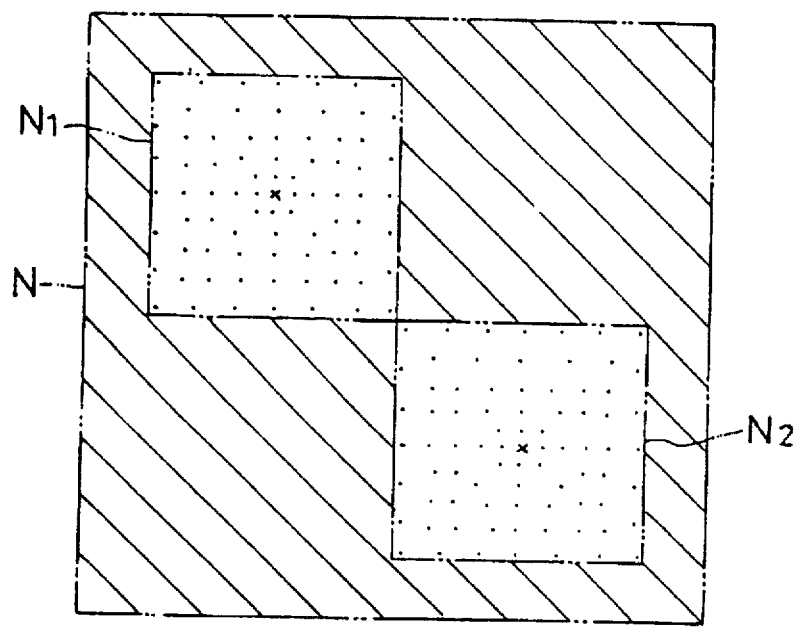
FIG. 8 is an explanatory view of lattice point movement in divided groups in the second embodiment.

The lattice points in each group are moved toward the lattice point having the greatest function value (current source size) (step S15). FIG. 8 shows how this step is taken. Reference N in FIG. 8 denotes the group of lattice points initially set at step S11. The lattice points marked "x" are the lattice points having a current source of the greatest value in the respective groups. The other lattice points in each group are moved toward this lattice point, to form a group of lattice points N1 or N2 lying closer together. The number of lattice points in the initial group N equals the total number of lattice points in the groups of lattice points N1 and N2. Step S15 of moving the other lattice points toward the lattice point having the greatest current source in each group is executed in the same way as in the first embodiment.

Step S16 is executed to check whether a minimum distance between lattice points in each group of lattice points N1 or N2 formed after the movement made at step S15 is less than a predetermined distance. This distance is determined as appropriate, based on the precision of deduced positions of the current sources.

In the first stage of group division, moving distances of the lattice points are set so that the minimum distance between the lattice points exceeds the predetermined value. Thus, the operation returns to step S12. The current sources of the rearranged lattice points are determined by the least norm method, regarding the groups of lattice points N1 and N2 as a new group of lattice points.

Figure 9:
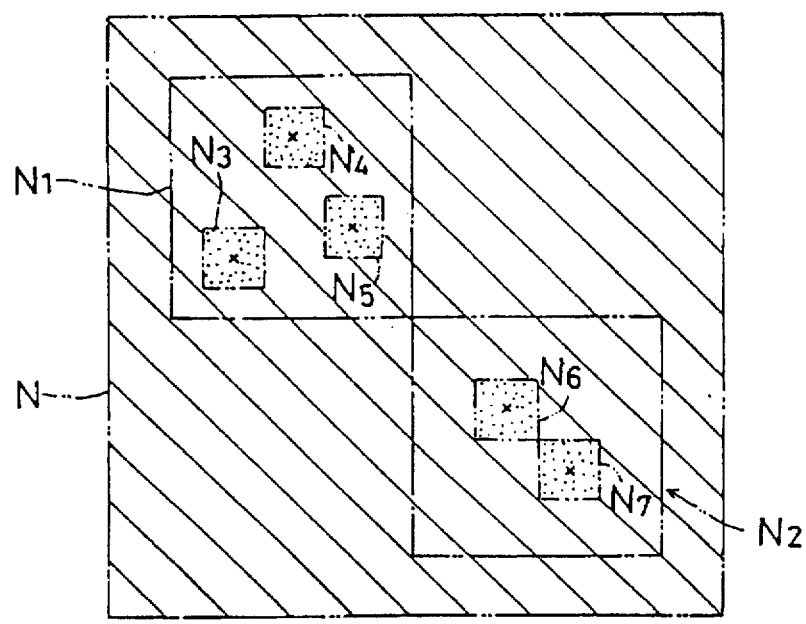
FIG. 9 is an explanatory view of lattice point movement in further divided groups in the second embodiment.

After the current source of each lattice point in the respective groups N1 and N2 is determined, the likelihood of presence at each lattice point of the current source is determined for the respective groups N1 and N2 as before (step S13). Then, the lattice points in each group N1 or N2 are further divided into groups (step S14). The lattice points in each group are moved (step S15). FIG. 9 shows new groups of lattice points N3 to N7 resulting from the above steps.

When, after repeating the above process, a minimum distance between lattice points is found to be below the predetermined value at step S16, the current sources of the group of lattice points determined at step S12 executed the last time are regarded as corresponding to the true current sources.

<simulation>

Figure 10A:
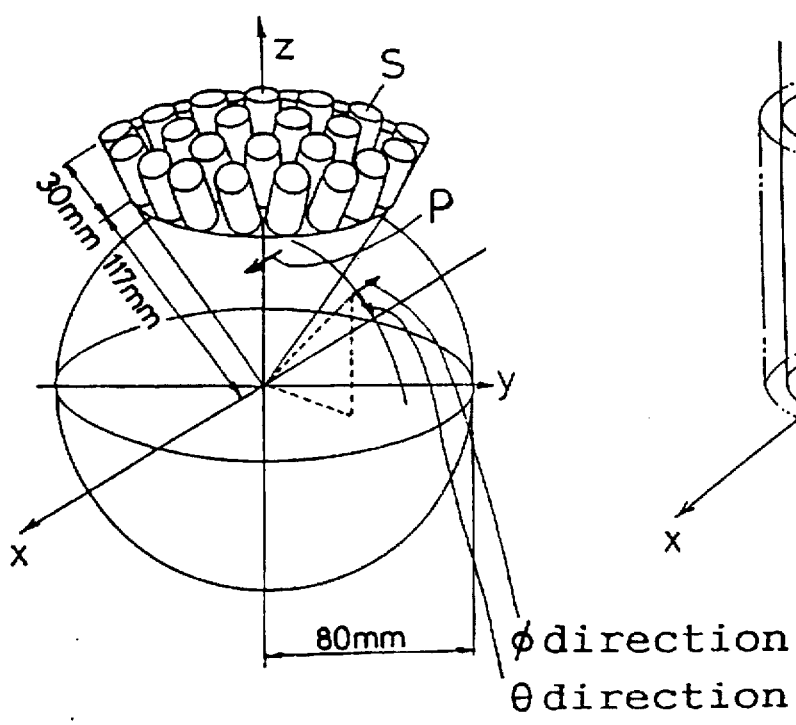
FIG. 10A is an explanatory view of a model used in a simulation of the second embodiment.

A simulation was carried out to ascertain validity of the above technique. A ball having an 80 mm radius was conceived as the head acting as the region for which current sources are deduced. As the magnetic sensors S, axial type linear differential gradiometers (see FIG. 10B) having a 30 mm base line were arranged in 37 channels over a spherical surface having a 117 mm radius. All the gradiometers had axes extending to the origin. Current dipoles (current sources) were set in the ball of the head, and the magnetic fields formed by the dipoles were calculated by means of Sarvas's equation (J. Sarvas, Phys. Med. Biol., vol. 32, pp 11–22, 1987) taking the effect of volume current into account. These magnetic fields were regarded as measured magnetic fields. FIG. 10A shows this model.

Next, the space was divided into lattices of 20 cubic millimeters, and 257 lattices lying within the ball of the head were used as objects of reconstruction. The sensors S used in this simulation extend in radial directions "r" of the ball, and therefore cannot detect magnetic fields formed by current components in the radial directions. Thus, deduction parameters were current components in $\theta$ directions and $\phi$ directions.

Figure 11A:
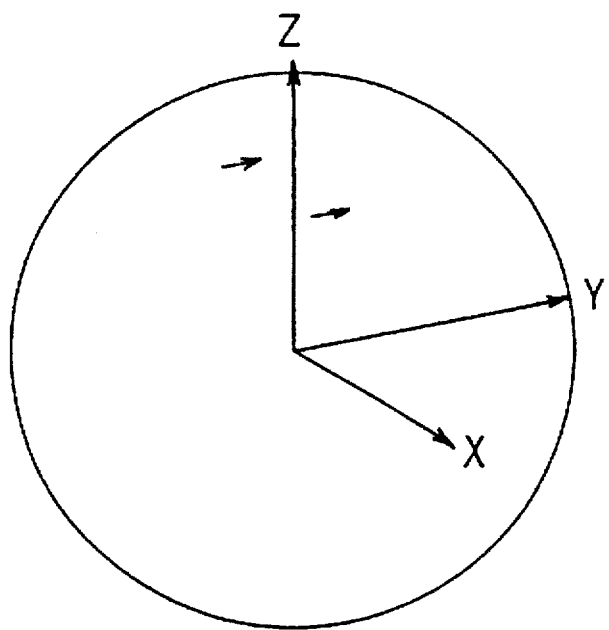
FIG. 11A is a view showing a setting of current sources in the simulation of the second embodiment.
Figure 11B:
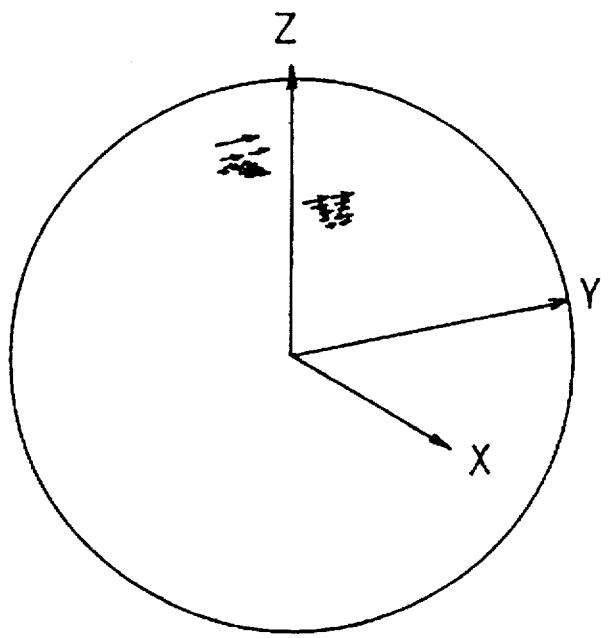
FIG. 11B is a view showing a reconstruction of the current sources shown in FIG. 11A.

The magnetic fields were computed on the assumption that two current dipoles acting as current sources had the same depth (20,0,50), (−30,0,50). The moment of both current dipoles were set to (0,10,0). The units are mm for the position, and nAm for the moment. The computed magnetic fields are regarded as measured values, and the results of deduction carried out in the above embodiment are shown in FIGS. 11A and 11B. FIG. 11A shows the setting, and FIG. 11B shows a reconstruction. While there are isolated current dipoles, the lattices gather around the true values, and the current dipoles are reconstructed in the right direction.

Figure 12A:
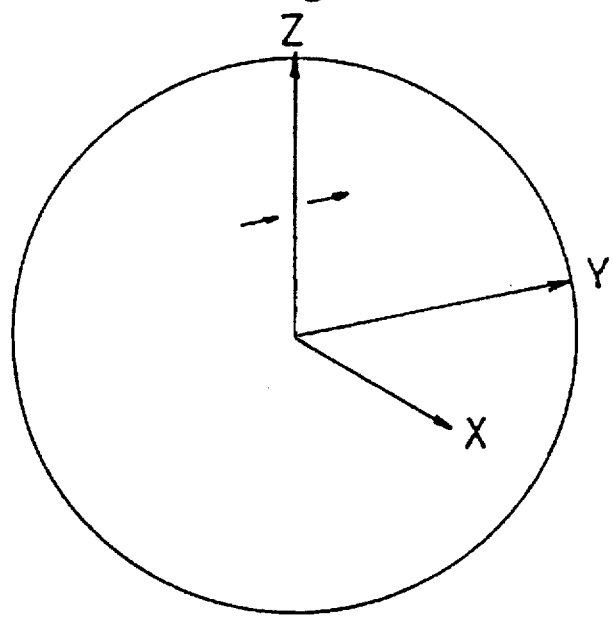
FIG. 12A is a view showing a different setting of current sources in the simulation of the second embodiment.
Figure 12B:
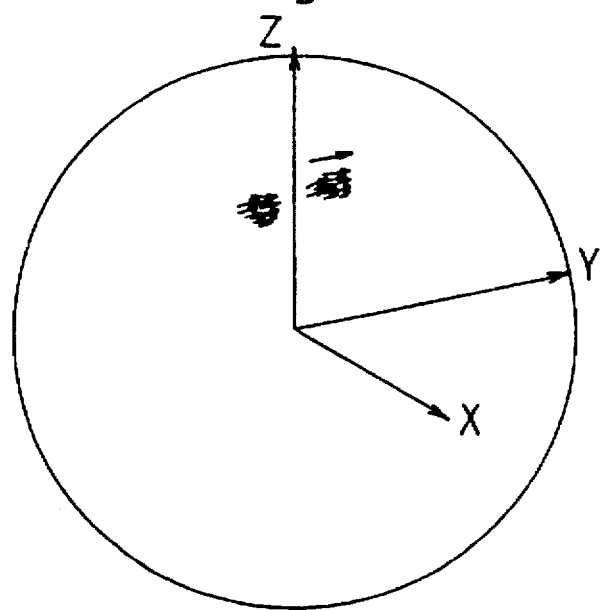
FIG. 12B is a view showing a reconstruction of the current sources shown in FIG. 12A.

Next, a case of setting the two current dipoles to different depths will be described. The current dipoles were set to positions (20,0,50) and (−20,0,30), and the moment was (0,10,0) for both. The results are shown in FIGS. 12A and 12B. FIG. 12A shows the setting, and FIG. 12B shows a reconstruction. While there are isolated current dipoles again, the current dipoles disposed at the different depths can also be reconstructed substantially correctly.

According to this embodiment, as understood from the foregoing description, likelihood of current sources being present on the lattice points is determined from the physical quantities of the current sources on the lattice points obtained by the least norm method. Based on the likelihood, the lattice points are divided into groups. The other lattice points are moved toward the lattice point having the current source of the greatest function value. The current sources of the rearranged lattice points are obtained by the least norm method. Thus, current sources are deduced by the least norm method, without increasing the number of lattice points. That is, the current sources may be deduced with high precision while maintaining the precision in computing the least norm solutions. Even if a plurality of true current sources are present, each current source may be deduced with high precision.

Third Embodiment

In what is known as the lattice point moving least norm method described in the second embodiment, the parameters, $\alpha$, $\beta$ and $\gamma$, must be set empirically. These parameters are dependent on the positions, sizes and orientations of the current sources. It is therefore difficult particularly for an operator having little experience to set proper values for the parameters based on isomagnetic field diagrams as described above. The parameters could be set improperly to produce results contrary to the true solution.

This embodiment obviates setting of parameters $\beta$ and $\gamma$, which relate to the likelihood of presence of the solution on each lattice point, among the above parameters $\alpha$, $\beta$ and $\gamma$, to deduce current sources with facility and precision.

Inventors have conducted intensive research and found that, by simultaneously measuring the three orthogonal components (i.e. vector measurement) of the magnetic field generated by each in vivo current source and by using this data in application of the above lattice point moving least norm method, the current sources may be deduced properly also by the following equation (9) in which parameter $\gamma$ in equation (7) is set to zero (obviating setting of parameter $\beta$ also):

$$Q(Vrj) = |VPj| \qquad (9)$$

It is believed that the current sources may be deduced properly also by equation (9) not including the second term of equation (7) for the following reason.

Figure 10B:
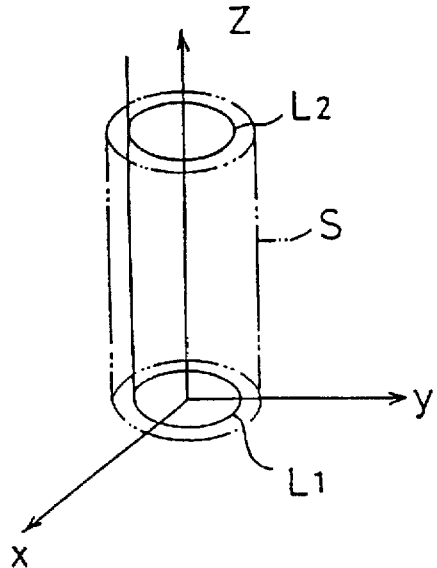
FIG. 10B is a schematic view of a magnetic sensor used in the simulation of the second embodiment.

Generally, as shown in FIG. 10A, the magnetic sensors S for detecting magnetic fields generated by in vivo current sources are arranged to have coil axes thereof extending radially where the area of the examinee M under examination is a spherical body. As shown in FIG. 10B, each magnetic sensor S has a pair of coils L1 and L2 arranged radially of the spherical body (in Z direction in FIG. 10B). Consequently, field data detected are Z-direction components only. Since only the Z-direction components are detected of the magnetic fields having three orthogonal X-, Y- and Z-direction components, the field data detected have a low degree of mutual independence to provide a low spatial resolving power. Thus, the second term in equation (7), i.e. the density of current sources adjacent the lattice points, is considered to have a great influence on likelihood Q of presence of solutions on the lattice points.

On the other hand, vector measurement of the magnetic fields generated by in vivo current sources detects the three orthogonal X-, Y- and Z-direction components of the magnetic fields in the examinee. The field data measured have an increased level of mutual independence to improve the spatial resolving power. It is thus believed that likelihood Q of presence of solutions on the lattice points is obtained with high precision from only the first term in equation (7), without taking the second term into account.

This embodiment will be described further with reference to the flowchart shown in FIG. 13.

The multichannel SQUID sensor 1 disposed adjacent the examinee M is driven to measure simultaneously the three orthogonal components of minute magnetic fields in the examinee M (vector measurement) (step S20). The magnetic sensors (pickup coils) S1 to Sm of the multichannel SQUID sensor 1 used here each comprise three pickup coils having detecting sensitivity in the three orthogonal directions. This type of pickup coil may be a three-axis gradiometer, for example. The gradiometer is formed by dividing the pickup coil into two opposite windings, to cancel uniform magnetic fields and detect only magnetic fields having gradients.

Figure 14:
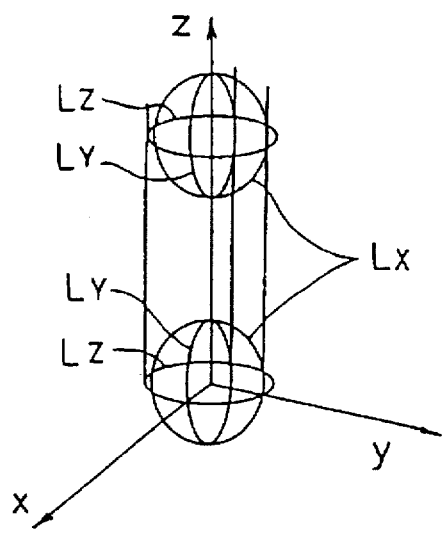
FIG. 14 is a schematic view of a magnetic sensor used in the third embodiment.

FIG. 14 schematically shows a construction of the three-axis gradiometer. The pickup coils LX, LY and LZ detect field components in X, Y and Z directions, respectively. The three-axis gradiometer is not limited to any particular construction. Three-axis coils may be attached to a cubic core element to be orthogonal to the six surfaces thereof. A three-axis gradiometer as disclosed in Japanese Patent Publication (Unexamined) No. 4-301581 may be used. The latter includes a cold temperature resistant flexible material rolled into a cylinder, and three pairs of superconducting film coils wound opposite and connected to each other and formed on surfaces of-the flexible material at varied angles to each other.

Next, three-dimensional lattice points N are set evenly in a region to be diagnosed, e.g. the brain (step S21). Then, a current source (least norm solution) at each lattice point is determined by the least norm method noted above (step S22).

Next, the likelihood of presence at each lattice point of the current source is determined using equation (9) described above (step S23).

To move lattice points having less likelihood toward lattice points of greater likelihood, the lattice points N are divided into groups by using group function $\phi$ expressed by equation (8) (step S24). Parameter (moving parameter) $\alpha$ in equation (8) is empirically selected as described hereinbefore.

Next, the lattice points in each group are moved minute distances toward the lattice point having the greatest function value (current source size) (step S25, see FIG. 8).

The next step S26 is executed to check whether a minimum distance between lattice points in each group of lattice points (N1 or N2 in FIG. 8) formed after the movement made at step S25 is less than a predetermined distance. This distance is determined as appropriate, based on the precision of deduced positions of the current sources.

In the first stage of group division, moving distances of the lattice points are set so that the minimum distance between the lattice points exceeds the predetermined value. Thus, the operation returns to step S22. The current sources of the rearranged lattice points are determined by the least norm method, regarding the groups of lattice points N1 and N2 as a new group of lattice points. After the current source of each lattice point in the respective groups N1 and N2 is determined, the likelihood of presence at each lattice point of the current source is determined for the respective groups N1 and N2 as before (step S23). Then, the lattice points in each group N1 or N2 are further divided into groups (step S24). The lattice points in each group are moved (step S25) to form new groups of lattice points (N3 to N7 in FIG. 9).

When, after repeating the above process, a minimum distance between lattice points is found to be below the predetermined value at step S26, the current sources of the group of lattice points determined at step S22 executed the last time are regarded as corresponding to the true current sources.

<simulation>

Simulations were carried out to ascertain validity of the above technique. Here, pickup coils as shown in FIG. 14 were assumed to make vector measurement. The pickup coils as shown in FIG. 10B were also used to measure only radial components, and magnetic field generated by the same current source were computed. To equalize the conditions for evaluating the two types of coils, the number of channels and the region for measurement were set substantially the same. For vector measurement, the channels were set to 13×3=39 channels, and the coil pitch to 37.5 mm. For radial measurement, the channels were set to 37 and the coil pitch to 25 mm. The coils were arranged on a ball having a 117 mm radius, with coil axes extending to the center of the ball. However, since tangential components of the magnetic fields are influenced by volume currents, the magnetic fields generated by the current sources were computed using a spherical model to take the influences of volume currents into account (J. Sarvas, Phys. Med. Biol., vol. 32, pp 11–22, 1987).

A deducing simulation was carried out, using equation (9), on each of the field data gained by vector measurement and radial measurement. A ball having an 80 mm radius was conceived as the head, and the magnetic sensors were arranged symmetrically about Z-axis (see FIG. 10A). The sensors were arranged at a distance of 37 mm from the surface of the ball. As the current sources, two current dipoles were arranged as follows:

| position [mm] | moment [nAm] |
|---|---|
| (20, 0, 50) | (0, 10, 0) |
| (−20, 0, 5) | (0, 10, 0) |

Figure 15A:
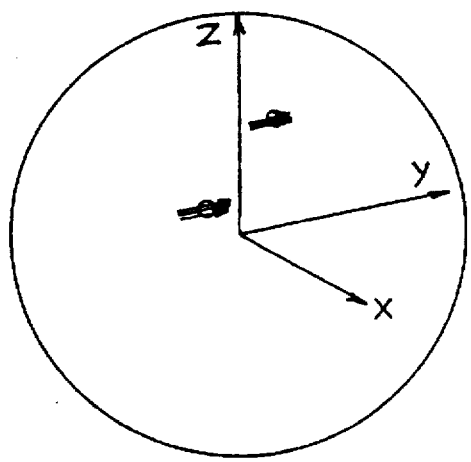
FIG. 15A is a view showing a reconstruction of current sources obtained in a simulation of the third embodiment.
Figure 15B:
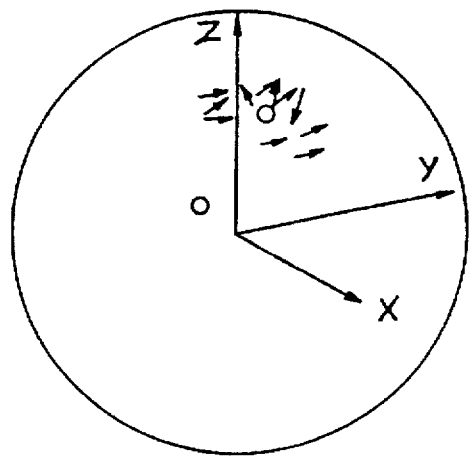
FIG. 15B is a view for comparison with FIG. 15A, and showing a reconstruction of current sources based on measurement in radial directions.

The results of deduction are shown in FIGS. 15A and 15B. FIG. 15A shows current sources deduced from the field data of vector measurement. FIG. 15B shows results of deduction based on the radial measurement. In the drawings, the circles show set positions of the current sources, and the arrows show deduced current sources. As seen from FIGS. 15A and 15B, the current sources are deduced correctly by the technique of this embodiment which applies the foregoing equation (9) to the field data obtained from the vector measurement, while the current sources are not deduced correctly where equation (9) is applied to the field data obtained from the radial measurement.

Thus, this embodiment requires empirical setting of only parameter α among parameters α, β and γ in the lattice point moving least norm method. The current sources may be deduced with so much facility and precision for the non-requirement for setting of parameters β and γ.

Fourth Embodiment

At step S24 in the third embodiment, parameter (moving parameter) α is set by experience of the operator. However, this moving parameter, depending on a value set thereto, could produce a totally different result. If this value can be determined by some means, a deduction technique of high generality requiring no empirical parameters may be realized in combination with the technique of the third embodiment described above.

Figure 16A:
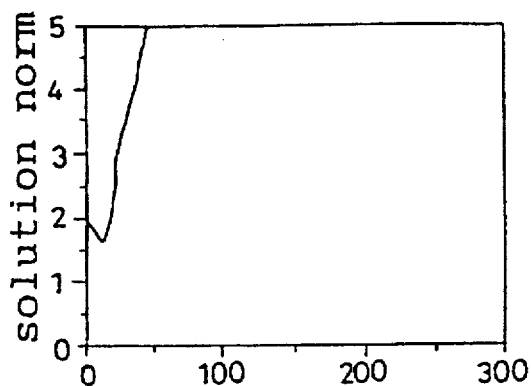
FIGS. 16A and 16B are views showing norm variations of solutions corresponding to moving parameter values.
Figure 16B:
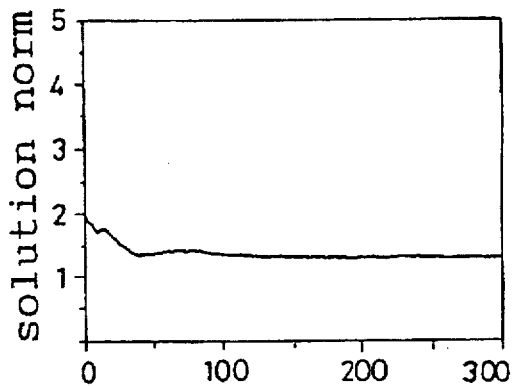
Figure 17A:
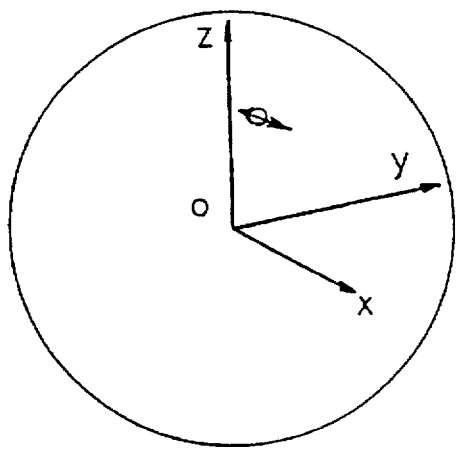
FIG. 17A is a view showing a reconstruction of current sources corresponding to FIG. 16A.
Figure 17B:
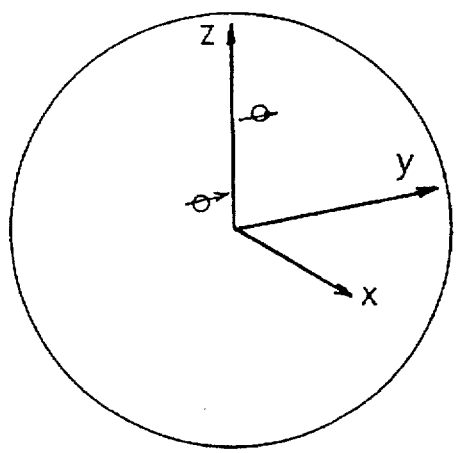
FIG. 17B is a view showing a reconstruction of current sources corresponding to FIG. 16B.

This embodiment regards the norm of the solution obtained by the least norm method as a criterion for determining moving parameter α. With this technique, the least norm solution is determined by moving the lattice points upon each repetition, and therefore the norm of the solution changes every time. Thus, variations in the norm of the solution were checked by setting various values to moving parameter α for deduction. Pickup coils for vector measurement as shown in FIG. 14 were used as sensors. The current sources and sensors were arranged as in the third embodiment. FIGS. 16A and 16B show norm variations where α is 0.3 and 0.5, respectively. In FIGS. 16A and 16B, the horizontal axis represents times of repetition, while the vertical axis represents solution norms. FIGS. 17A and 17B show results of deduction thereof. When α is 0.3, the norm of the solution diverges as shown in FIG. 16A, and produces different deduction results as shown in FIG. 17A. When α is 0.5, the norm of the solution converges as shown in FIG. 16B, and produces proper deduction results as shown in FIG. 17B.

These facts show that optimal moving parameter α may be determined by obtaining lattice point moving parameter α to minimize the norm of the solution, and moving the lattice points based on this parameter upon each repetition.

A sequence of current source deduction using automatic adjustment of moving parameter α will be described hereinafter with reference to the flowchart shown in FIG. 18.

Figure 18:
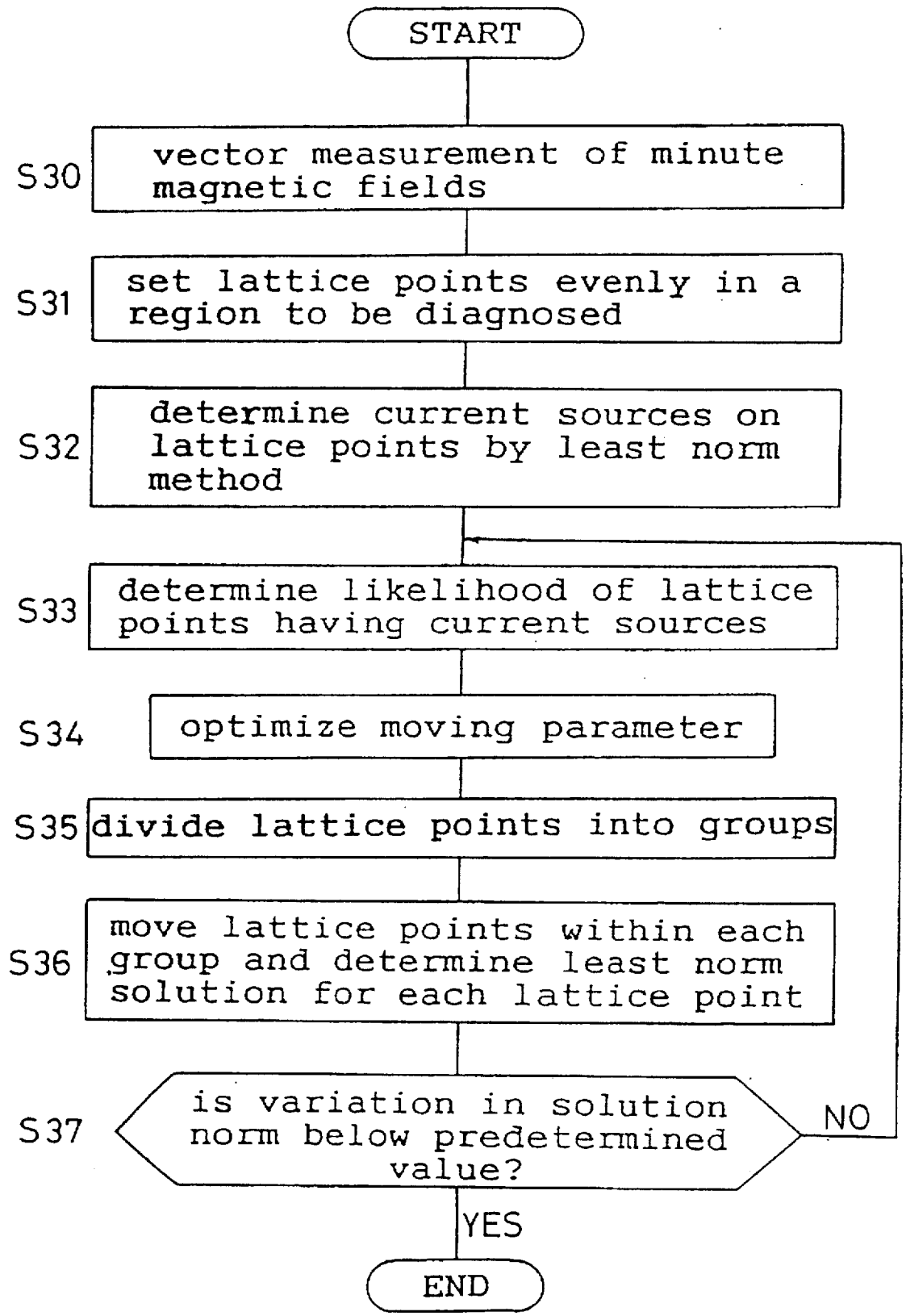
FIG. 18 is a flowchart of current source deduction processing in a fourth embodiment.

Steps S30–S33 in FIG. 18 are the same as steps S20–S23 of the third embodiment shown in FIG. 13, and will not be described again.

At step S34, before dividing the lattice points into groups by using the foregoing equation (8) at step S35, moving parameter α is optimized by using evaluation function "f" expressed by the following equation (10):

$$f(\alpha) = \sum_{j=1}^{n} |Vpj(\alpha)| \qquad (10)$$

In equation (10), VPj(α) is a solution obtained by the least norm method after moving the lattice points by using moving parameter α. Thus, evaluation function "f" is the norm of the solution. Further, "n" represents the number of lattice points.

At steps S34 to S36, several parameters α1, α2, α3 and so on are applied in advance, the lattice points are tentatively moved by using these parameters, and the least norm solutions are obtained, respectively. These least norm solutions are applied to equation (10) to derive values of evaluation functions f(α1), f(α2), f(α3) and so on. The parameter having the least value is adopted as moving parameter α. The least norm solution obtained by moving the lattice points based on the adopted moving parameter α is adopted, and the least norm solutions based on the other parameters are discarded.

Then, step S37 is executed to determine an amount of variation Δf between the norm of the solution (evaluation function value $f_{L-1}$) derived from steps S33 to S36 executed the previous time and the norm of the solution (evaluation function value $f_L$) derived from these steps executed this time. If this amount of variation Δf is below a predetermined value, the repetition is terminated. Otherwise, the operation returns to step S33. Steps S33–S36 are repeated until the amount of variation Δf falls below the predetermined value.

The technique illustrated in FIG. 18 not only requires no empirical parameters α, β or γ but employs the norm of the least norm solution as the condition to stop the repetition (step S37). Thus, the current source deduction processing may be stopped after an appropriate number of repetitions.

<simulation>

A simulation was carried out to ascertain validity of the technique of automatically adjusting moving parameter α. Nineteen pickup coils as shown in FIG. 14 were arranged on a spherical surface to make vector measurement. Thus, the number of channels was 19×3=57. The coil pitch was set to 25 mm on the spherical surface having a 131 mm radius. The head was regarded as a ball having a 80 mm radius, and the magnetic fields were computed taking the effect of volume currents into account. The sensors were arranged symmetrically about Z-axis, at a distance of 36 mm from the ball of the head. As the current sources, a plurality of current dipoles were arranged.

The cerebral cortex was assumed to lie inside the head ball, and three current dipoles were set thereon. The position and moment of each current dipole are as follows:

| position [mm] | moment [nAm] |
|---|---|
| (−27.08, 4.78, 47.63) | (−8.53, 1.50, −5.00) |
| (−27.08, −4.78, 47.63) | (−8.53, −1.50, −5.00) |
| (4.91, −56.08, 32.50) | (0.44, −4.98, −8.66) |

Figure 19:
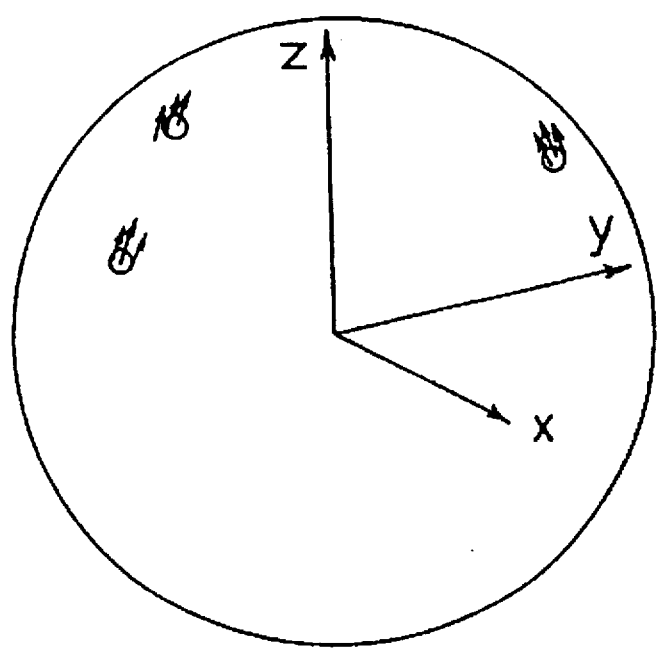
FIG. 19 is a view showing a reconstruction of current sources obtained in a simulation of the fourth embodiment.

FIG. 19 shows the results of current source deduction carried out by the lattice point moving least norm method while automatically adjusting moving parameter α. As seen, the current sources are deduced adjacent proper positions. In deducing the current sources by this technique, a solution is obtained as a distribution of current dipoles even if the true current source comprises a single current dipole. When the moments of the current dipoles are integrated, the value substantially corresponds to the set moment of the current dipoles, which confirms validity of this technique.

According to this embodiment, as understood from the foregoing description, the three orthogonal components of the current sources generated by bioelectric currents are detected simultaneously by a plurality of magnetic sensors. In the lattice point moving least norm method, therefore, the likelihood of current sources being present at the lattice points is determined by considering the sizes of the current sources at the lattice points. There is no need for considering density of the current sources around each lattice point. It is therefore unnecessary to empirically set parameters for determining levels of influences of the density of the current sources around each lattice point on the likelihood of current sources being present at the lattice points. The current sources may be deduced with facility and precision accordingly.

Fifth Embodiment

The least norm method described above is based on the premise that the number of unknowns 3n (n being the number of lattice points), where the sizes in X, Y and Z directions of the current sources assumed for the respective lattice points are taken into account, is greater than the number of magnetic sensors m (the number of equations), i.e. 3n>m. Consequently, coefficient matrix A in the foregoing equation (2) could be lowered in level (i.e. the same column vector could appear). This renders the solutions derived unstable.

Further, the least norm method is added only as a condition for solving simultaneous equation (2). No clear theoretical basis is provided for minimizing norm |P| of current source [P]. It is therefore difficult to conclude whether or not the current sources deduced by this method represent a substantially true current source.

In the lattice point moving least norm methods proposed in the first and second embodiments also, whether a minimum distance between lattice points is below a predetermined convergent criterion is used as a convergent determination condition for deducing final current sources in the course of repeating movement of the lattice points and the least norm method. Thus, deduction results could vary with the predetermined convergent criterion. This poses a problem of impairing generality of the deduction method.

This embodiment eliminates the above disadvantages. Specifically, this embodiment realizes greater accuracy in deducing current sources, requires no convergent criterion to be set for deduction of current sources, and enables a final deduction of current sources to be effected uniformly.

Figure 20:
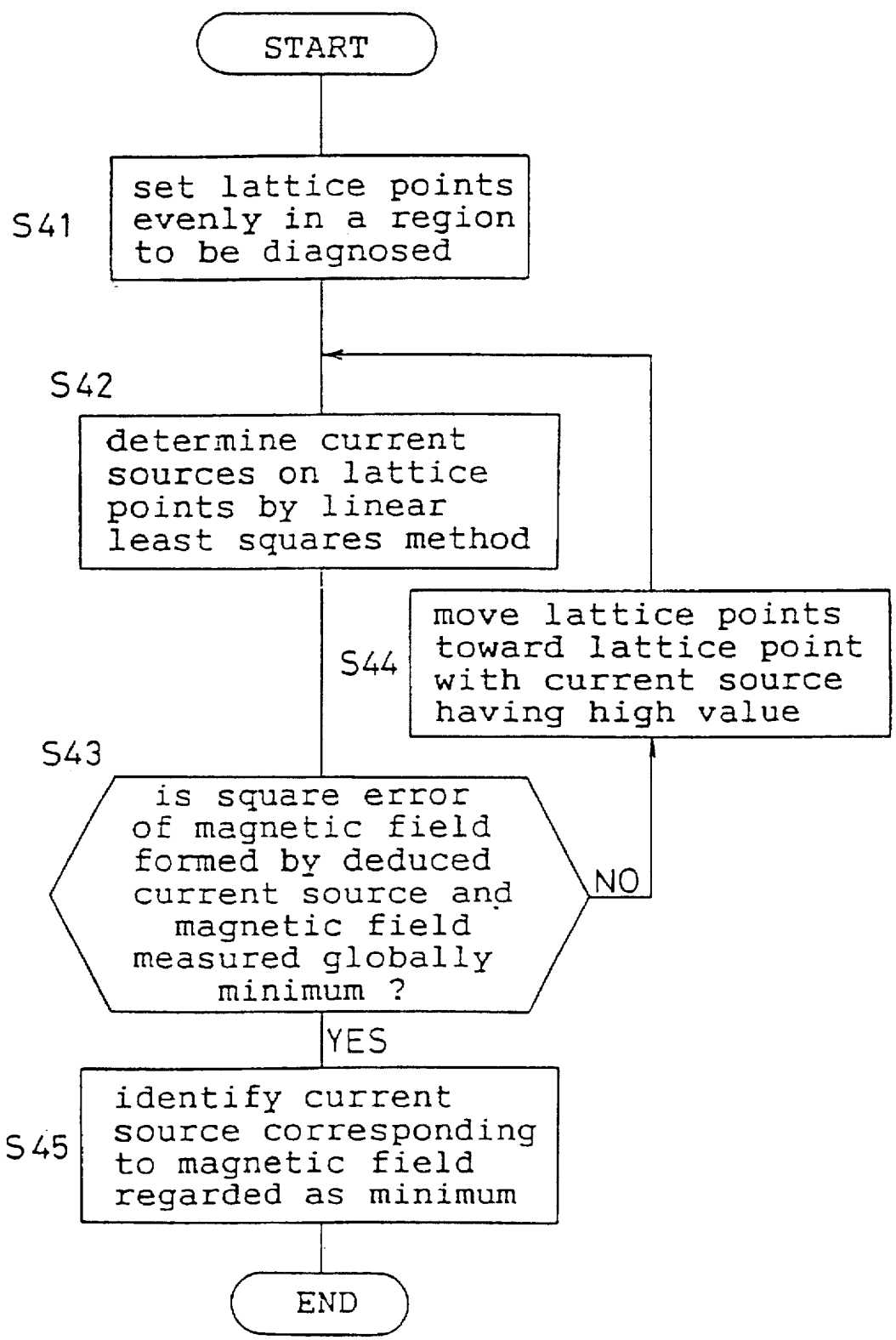
FIG. 20 is a flowchart of current source deduction processing in a fifth embodiment.

In this embodiment, field data are collected from the examinee M by the same multichannel SQUID sensor 1 as used in the first and second embodiments. A sequence of current source deduction will be described hereinafter with reference to the flowchart shown in FIG. 20.

First, three-dimensional lattice points N are set evenly in a region to be diagnosed, e.g. the brain (step S41). Here, the number of lattice points N is selected so that the number of unknowns 3n is smaller than the number of magnetic sensors S1–Sm. This enables current sources [P] to be derived by a linear least squares method as described later.

Next, step S42 is executed to determine current sources [P] from magnetic fields [Bd] detected by the magnetic sensors S1–Sm. The current sources [P] and magnetic fields [Bd] are in the following relationship as in the foregoing equation (2):

$$[Bd]=A[P]$$

As noted hereinbefore, matrix A includes coefficient $\alpha_{ij}$ representing intensity of a magnetic field detected in the position of each magnetic sensor S1 to Sm, where the current sources of unit sizes in X, Y and Z directions are arranged on the lattice points. Matrix A has 3n×m elements. Thus, current sources [P] can be derived from;

$$[P]=A^{-1}[Bd]$$

as expressed by the foregoing equation (4). However, no solution is available if the number of equations m (the number of magnetic sensors S1–Sm) is greater than the number of unknowns 3n (the number of current sources assumed for the lattice points). Then, by adding a condition to minimize square error |[Bd]−[B]| between measured magnetic fields [Bd] and current sources [B] applied to the magnetic sensors S1–Sm by current sources [P] assumed for the respective lattice points, current sources [P] may be derived from the following equation using the well-known linear least squares method to minimize the square error:

$$[P]=(A'A)^{-1}A'[Bd]$$

Next, at step S43, the magnetic fields applied to the magnetic sensors S1–Sm by current sources [P] obtained by the linear least squares method at step S42 are derived from the foregoing equation (2), i.e.:

$$[B]=A[P]$$

Square error |[Bd]−[B]| between these magnetic fields and the magnetic fields actually detected by the magnetic sensors S1–Sm are computed, and the square error is checked whether it is a global minimum or not.

If the square error is a global minimum, it means that the value is the least among the least square errors obtained by the above method for the positions of the respective lattice points when the lattice points are moved plural times during repetition of step S44 described later. Whether the square error is a global minimum or not may be determined by storing the least square errors obtained by the method of above steps S42 and S43 for the lattice points successively moved in the course of repeating step S44 as described later, and comparing these square errors to find a global minimum thereamong. Thus, when the square error obtained is found not to be a minimum at step S43, the operation proceeds to step S44 to move the lattice points. If the square error is found to be a minimum, the operation proceeds to step S45 to finally deduce current sources [P].

At step S44, the lattice points are divided into a plurality of groups and moved based on the likelihood of a current source being present at each lattice point. Computation of the likelihood of a current source being present at each lattice point, and division into groups and movement of the lattice points based thereon, are carried out using equations (7) and (8) as in the second embodiment, and will not be described again.

After moving the lattice points, the operation returns to step S42 to obtain current sources [P} for the moved lattice points. This and previous computations are different in coefficients of matrix A identified by the position of each lattice point. Step S43 is executed again to determine whether the square error is a minimum or not. If the square error is found not to be a minimum, steps S42–S44 are repeated. If the square error is found to be a minimum, step S45 is executed to regard current sources [P] providing the minimum current source [B] as the true current source. This completes the processing sequence.

<simulation>

Figure 21:
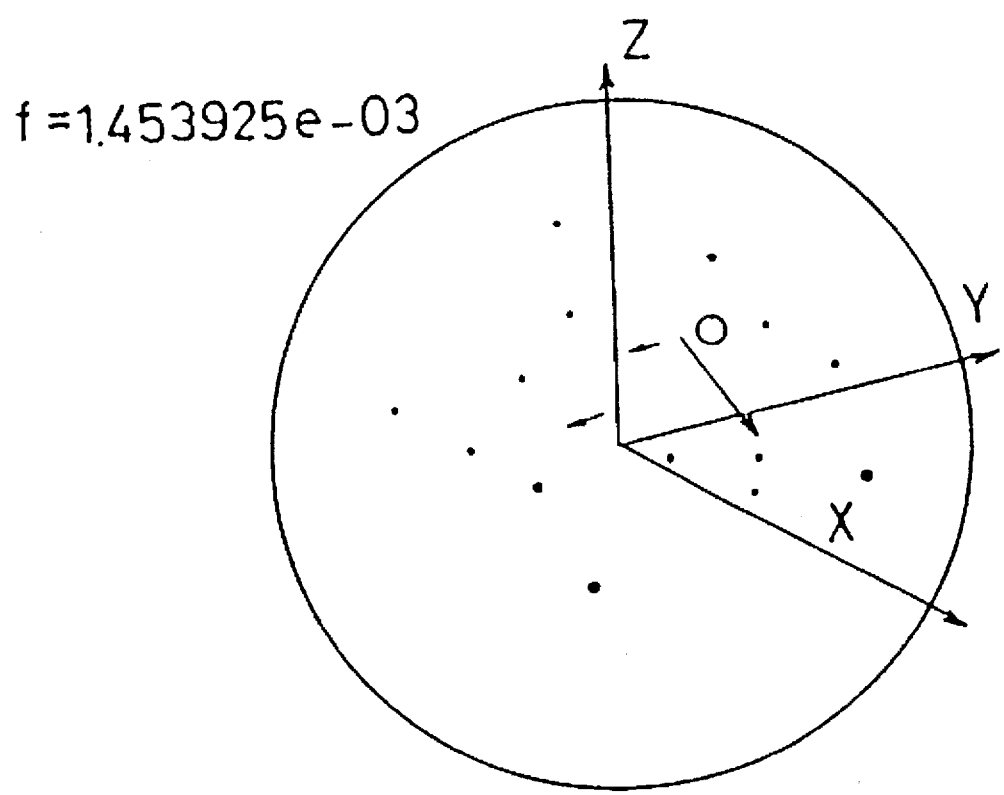
FIGS. 21, 22 and 23 are views showing reconstructions in different stages of current sources obtained in a simulation of the fifth embodiment.
Figure 22:
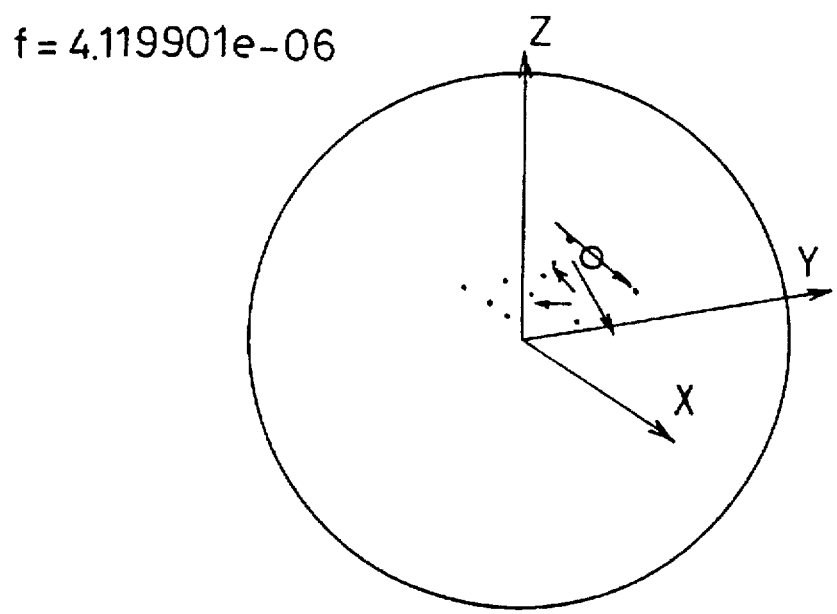
Figure 23:
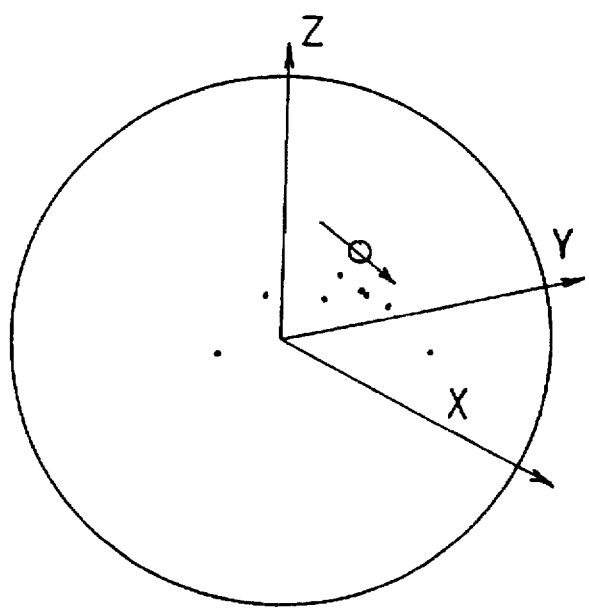

A simulation was carried out to ascertain functions of the above technique visually. FIGS. 21 through 23 show a three-dimensional arrangement of lattice points, assuming that the number of lattice points n is 28, and the number of magnetic sensors m is 129. It is further assumed that a current source (5.6, 5.6, −6.0) [nAm] is present in the position marked with a circle (16.0, 16.0, 30.0) [mm]. The arrows and black spots indicate the lattice points. Lattice points having large current values are indicated by large black spots. Lattice points having larger current values are indicated by the arrows. Lattice points having small current values do not appear in these drawings. Thus, the drawings show fewer lattice points than the actual number thereof.

FIG. 21 shows current sources [P] deduced immediately after the lattice points were set evenly. The square error was f=1.454925e$^{-03}$ at this time. FIG. 22 shows current sources [P] after the lattice points were moved plural times. It will be seen that, compared with FIG. 21, the lattice points have been collected around the true current source. The lattice points having large current values as indicated by the arrows appear adjacent the true current source. The square error was f=4.119901e$^{-06}$ at this time. FIG. 23 shows positions of the current sources when the square error is minimized. The plurality of lattice points having large current values as indicated by the arrows in FIG. 22 now overlap the true current source, showing that the true current source is deduced correctly.

As described above, this embodiment employs the magnetic sensors larger in number than the unknowns corresponding to the set lattice points. Thus, stable solutions (current sources [P]) are derived from the magnetic fields [Bd] measured by the magnetic sensors.

The current sources are derived from the measured magnetic fields on condition that the square error between the magnetic fields [B] due to unknown current sources [P] at the lattice points and the magnetic fields [Bd] measured by the magnetic sensors is minimized. This allows the current sources [P] to be deduced accurately. In addition, the current sources [P] occurring when this square error is a global minimum is regarded as the true current source. It is therefore unnecessary to set a convergent criterion for deducing final current sources, thereby allowing a uniform deduction of final current sources.

Sixth Embodiment

The fifth embodiment described above uses group functions, and therefore requires parameters to be set for deduction of current sources. Further, since the lattice points are moved little by little within each group, the lattice points are moved a large number of times and a considerable time is consumed in computation before results of deduction are produced. This embodiment overcomes these disadvantages of the fifth embodiment. This embodiment requires no parameter setting, and moves the lattice points at a time, to allow current sources to be deduced in a short time.

Figure 24:
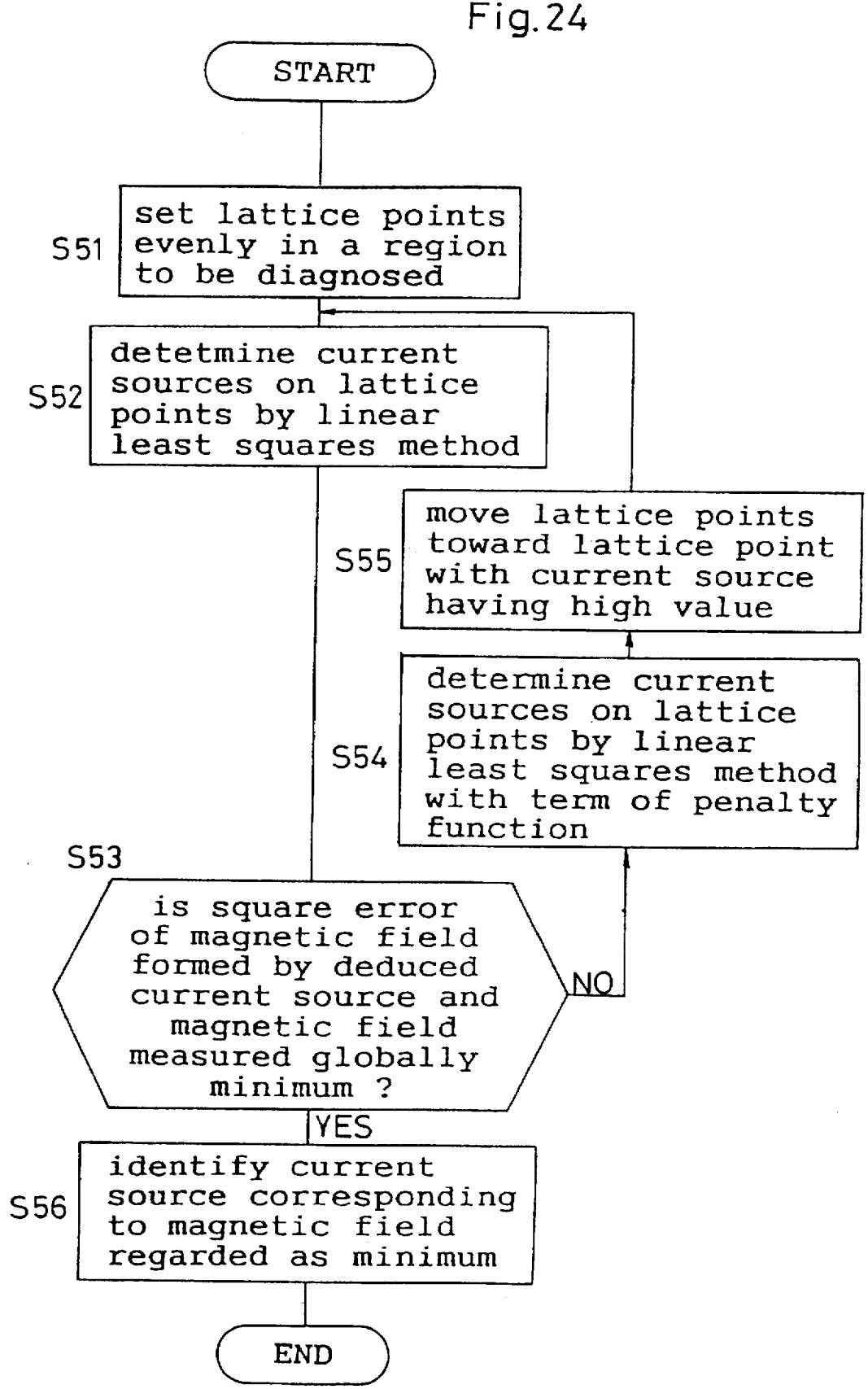
FIG. 24 is a flowchart of current source deduction processing in a sixth embodiment.

This embodiment will be described hereinafter with reference to the flowchart shown in FIG. 24.

First, at step S51, lattice points are set evenly in a region to be diagnosed, as in the fifth embodiment. Then, step S52 is executed to determine unknown current sources [P] at the respective lattice points by the least norm method. At step S53, the square error between magnetic fields [B] derived from the current sources [P] obtained at step S52 and magnetic fields [Bd] actually detected by the magnetic sensors S1–Sm is checked whether it is a global minimum or not.

If the square error is found not to be a global minimum at step S53, the operation proceeds to step S54 for newly determining current sources at the lattice points under the condition to minimize evaluation function f to which a penalty term is added as follows:

$$f = \sum_{i=1}^{n} (Bdi - Bi)^2 + \lambda \sum_{i=1}^{3m} (wi \cdot Pi^2) \quad (11)$$

In this case, A$^+$ in equation (5), [P]=A$^+$[B], can be derived from the following equation (12):

$$A^+ = (A'A + \lambda \cdot W)^{-1} \cdot A' \quad (12)$$

where $$W = \begin{pmatrix} w1 & & & & \\ & w2 & & 0 & \\ & & w3 & & \\ & & & \cdot & \\ & & & & \cdot \\ & 0 & & & \cdot \\ & & & & w3n \end{pmatrix} \quad (13)$$

Generally, the closer current source Pi is to a field measuring plane, the greater current source is measured. Thus, by setting matrix W as follows, for example;

$$Wi = \sum_{j=1}^{m} Aji^2 \quad (14)$$

the influence of the distance to the field measuring plane may be canceled for current source Pi derived. Further, the term of the square error of magnetic fields (A'A) and the penalty term (W) may be substantially equalized by setting weight λ of the penalty term to |A'A|/|W|.

Thus, current sources P on the respective lattice points are derived from equations (5) and (12). At step S55, the lattice points are moved to the vicinity of the lattice point having the greatest of the current sources P determined at step S54. In the mode of movement employed here, without being limitative, eight lattice points having small currents deduced are moved to the corners of a cube with the lattice point of the greatest current deduced lying in the center thereof. The cube has a size corresponding to a half of the distance between the lattice point of the greatest current deduced and the lattice point closest thereto.

After moving the lattice points in the above sequence, the operation returns to step S52 for newly obtaining current sources [P} for the moved lattice points. Then, step S53 is executed again to determine whether the square error is a global minimum or not. If the square error is found not to be a minimum, steps S52–S55 are repeated. If the square error is found to be a global minimum at step S53, step S56 is executed to regard current source [P] providing the globally minimum current source [B] as the true current source. This completes the processing sequence.

According to this embodiment, current sources are determined invariably by using the evaluation function in moving the current sources at the lattice points. The greatest current source may be determined by a simplified sequence. Further, since the penalty term which is a weighted sum of squares of the current sources is added to the evaluation function, stable solutions are obtained even where the lattice points are not in the true current source. This allows the lattice points to be moved at a time to the vicinity of the greatest current source. The greatest current source may be determined without using the group function described in the fifth embodiment. Consequently, this embodiment dispenses with a complicated sequence, for example, of setting parameters for deducing the current sources. In the fifth embodiment, the lattice points are moved little by little within each group. Consequently, the lattice points are moved a large number of times and a considerable time is consumed in computation before results are produced. In the sixth embodiment, as described above, the lattice points are moved at a time, thereby allowing the current sources to be deduced in a short time.

<simulation>

Figure 25:
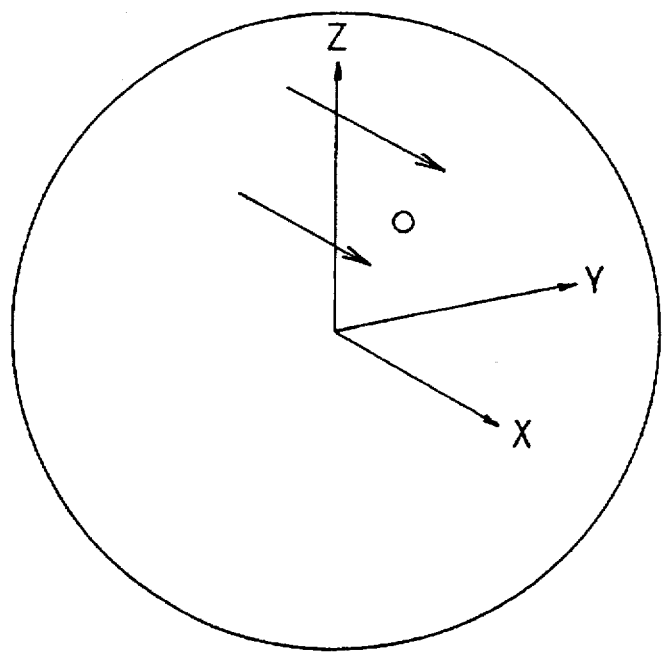
FIG. 25 is a view showing a reconstruction of current sources obtained by improper parameter setting, for comparison with the sixth embodiment.
Figure 26:
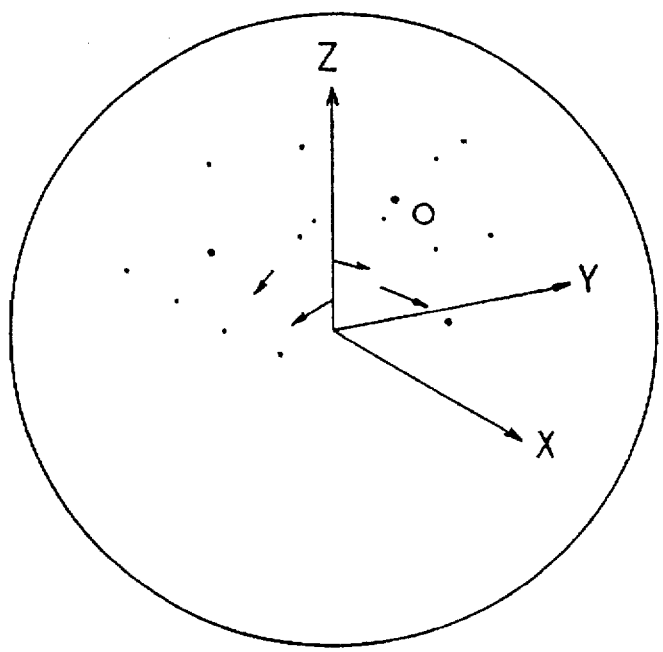
FIG. 26 is a view showing a reconstruction of current sources obtained without using a penalty term, for comparison with the sixth embodiment.
Figure 27:
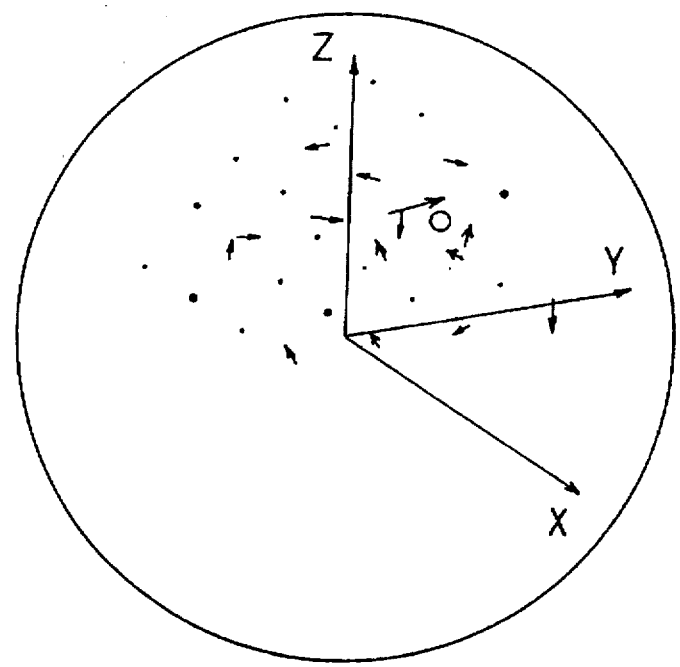
FIGS. 27, 28 and 29 are views showing reconstructions in different stages of current sources obtained in a simulation of the sixth embodiment.
Figure 28:
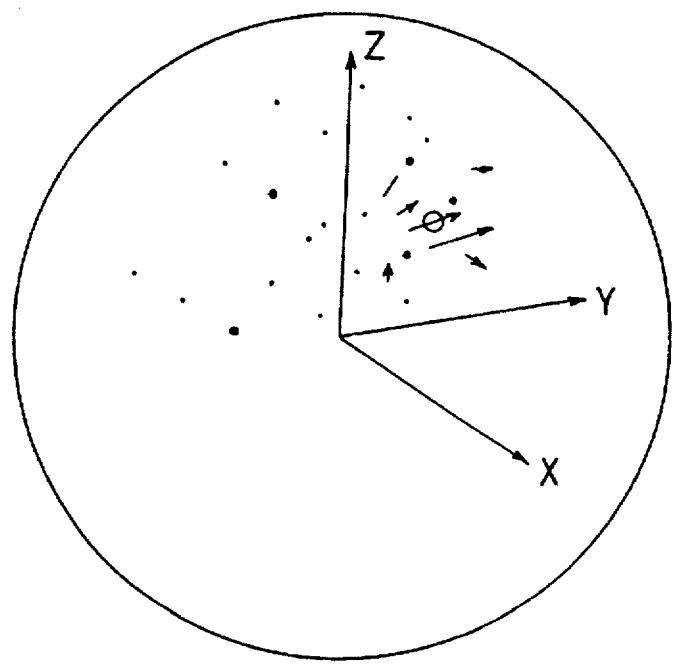
Figure 29:
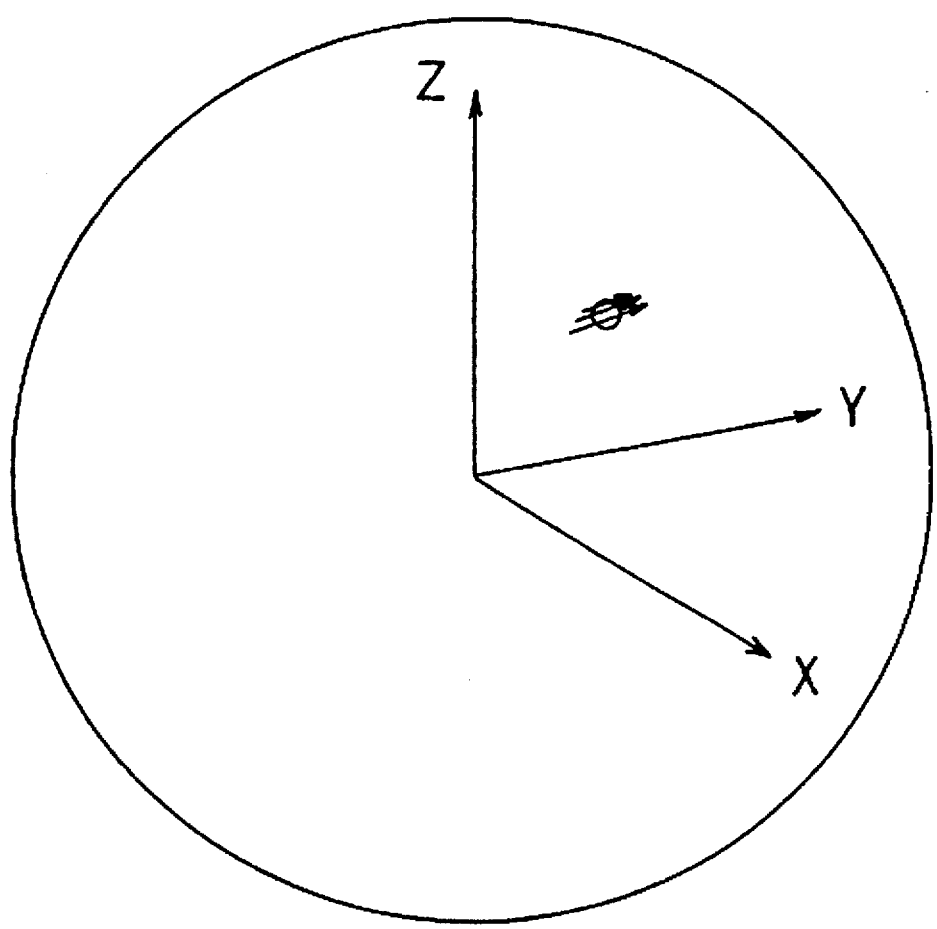

Simulations were carried out to ascertain functions of the above technique visually. FIG. 25 shows results of a simulation of the fifth embodiment for which improper parameter setting is assumed. FIG. 26 shows results of current source deduction done with the penalty term removed from the evaluation function in equation (11) noted above. FIGS. 27 through 29 are results of the simulation showing the current sources deduced in the sixth embodiment. Each of FIGS. 25 through 29 shows a three-dimensional arrangement of lattice points, assuming that the number of lattice points n is 32 and the number of magnetic sensors m is 129, and that a current source $(-10\sqrt{2}, 10\sqrt{2}, 0)$ [nAm] is present in the position marked with a circle (16.0, 16.0, 60.0) [mm]. The arrows and black spots indicate the lattice points. Lattice points having large current values are indicated by large black spots. Lattice points having larger current values are indicated by the arrows. Lattice points having small current values do not appear in these drawings. Thus, the drawings show fewer lattice points than the actual number thereof, i.e. 32.

As shown in FIG. 25, the true current source is not deduced correctly if wrong parameter setting is made in the fifth embodiment. According to the sixth embodiment, as shown in FIGS. 27 through 29, as the lattice points are moved repeatedly, a plurality of current sources seen in FIG. 27 approach the true current source, and ultimately overlap the true current source as shown in FIG. 29, thereby allowing the true current source to be deduced correctly.

Seventh Embodiment

The fifth and sixth embodiments described above determine current sources at the respective lattice points by the linear least squares method. If noise mixes into the magnetic fields measured, noise components may also be calculated as solutions (current sources). This results in the disadvantage that the position of each current source deduced tends to vary. This embodiment is intended to eliminate the instability due to such noise components.

Figure 30:
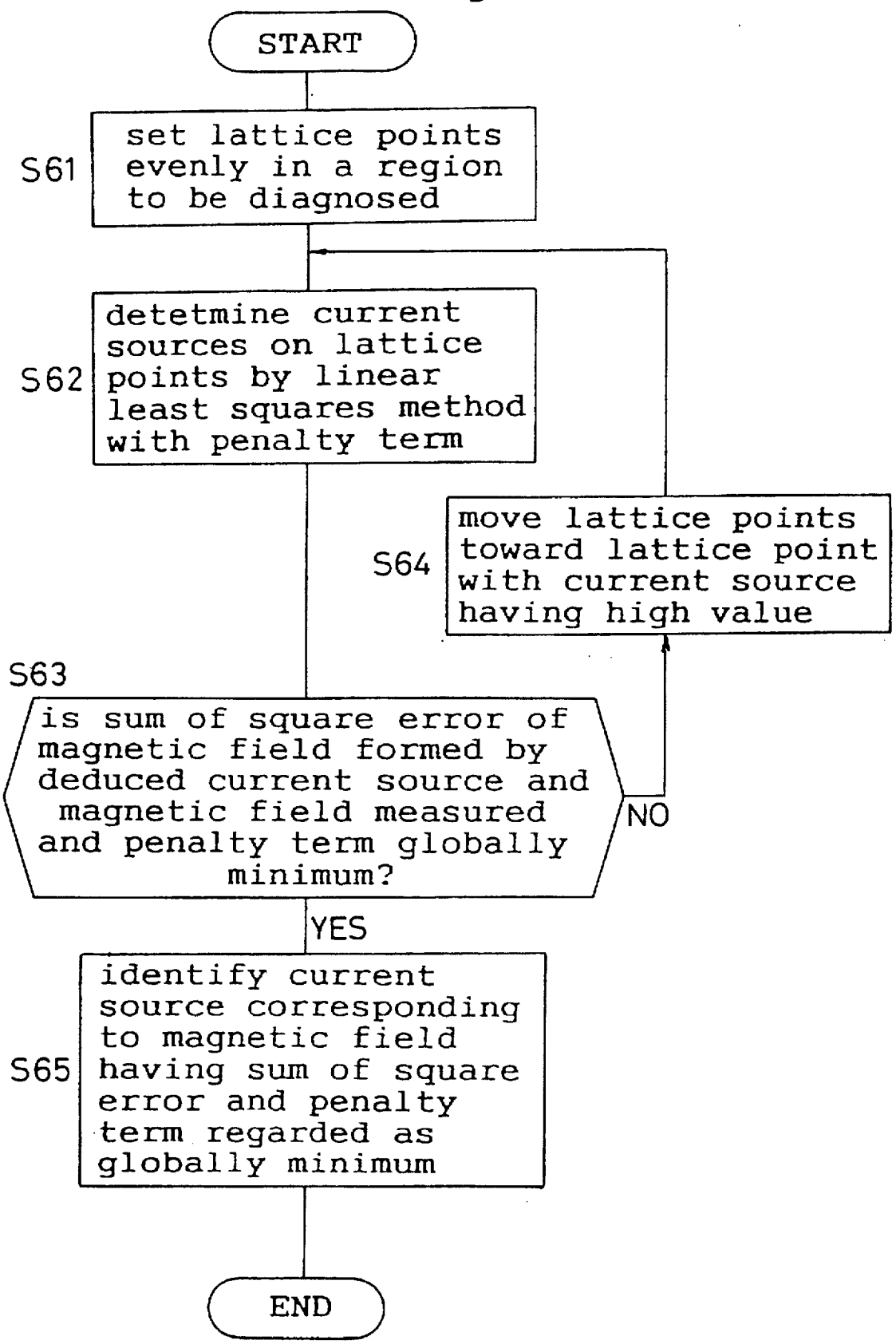
FIG. 30 is a flowchart of current source deduction processing in a seventh embodiment.

This embodiment will be described hereinafter with reference to the flowchart shown in FIG. 30.

At step S61, three-dimensional lattice points N are set evenly in a region to be diagnosed, e.g. the brain, as in the fifth and sixth embodiments. Here again, the number of lattice points N is selected so that the number of unknowns 3n is smaller than the number of magnetic sensors S1–Sm.

Next, step S62 is executed to determine current sources [P] from magnetic fields [Bd] detected by the magnetic sensors S1–Sm, using equation (4) noted hereinbefore.

$$[P]=A^-[Bd] \quad (4)$$

Matrix A includes 3n×m elements as expressed by equation (3) also noted hereinbefore.

With equation (4), no solution is available since the number of equations m (the number of magnetic sensors S1–Sm) is greater than the number of unknowns 3n (the number of current sources assumed for the lattice points). Thus, current sources [P] are derived using the linear least squares method by adding a condition to minimize evaluation function f expressed by a sum of square error $|[Bd]-[B]|$ between measured magnetic fields [Bd] and current sources [B] applied to the magnetic sensors S1–Sm by current sources [P] assumed for the respective lattice points, and the penalty term shown hereunder. This evaluation function is the same as equation (11) described in the sixth embodiment, which is set out below again.

$$f = \sum_{i=1}^{n} (Bdi - Bi)^2 + \lambda \sum_{i=1}^{3m} (wi \cdot Pi^2) \quad (11)$$

By adding the condition to minimize evaluation function f, equation (4) is rewritten as:

$$[P]=A^+[B] \quad (5)$$

$A^+$ can be derived from equation (12) described in the sixth embodiment.

The second, penalty term in equation (11) has the smaller value, the closer the current sources lie to one another. Consequently, noise components occurring discretely have no chance of being adopted as solutions.

After current sources [P] are determined, step S63 is executed to check whether the sum of square error between current sources [B] applied to the magnetic sensors S1–Sm by current sources [P] assumed and measured magnetic fields [Bd], and the above penalty term, is a global minimum or not. If the sum is found not to be a global minimum, the operation proceeds to step S64 for moving the lattice points to the vicinity of the lattice point having the greatest of current sources [P] obtained at step S62.

After moving the lattice points, the operation returns to step S62 for newly obtaining current sources [P] for the moved lattice points by the linear least squares method, adding the condition to minimize the evaluation function as noted above. Then, step S63 is executed again to determine whether the sum of the square error and penalty term is a global minimum or not. If the sum is found not to be a minimum, steps S62–S64 are repeated. If the sum is found to be a global minimum at step S63, step S65 is executed to regard current source [P] providing the globally minimum current source [B] as the true current source. This completes the processing sequence.

<simulation>

Figure 31:
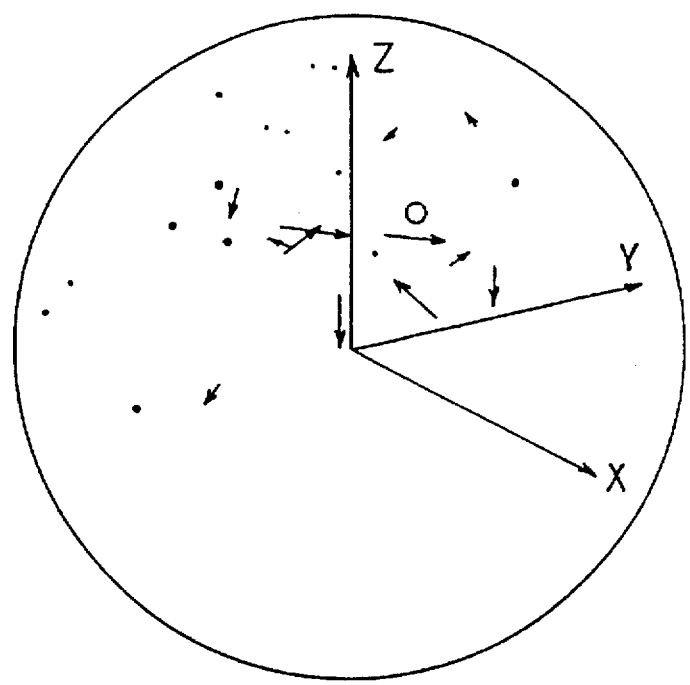
FIG. 31 is a view showing a reconstruction of current sources obtained from the sixth embodiment, for comparison purposes.

Simulations were carried out to ascertain functions of the above technique visually. FIG. 31 shows results of a simulation of the foregoing sixth embodiment which assumes that a current sources $(-10\sqrt{2}, 10\sqrt{2}, 0)$ [nAm] is present in the position (16.0, 16.0, 48.0) [mm], and 32 lattice points are set to magnetic fields determined by measuring these current sources with 129 magnetic sensors (with a signal to noise ratio=20). According to the sixth embodiment, the current sources obtained are scattered under the influence of noise.

Figure 32:
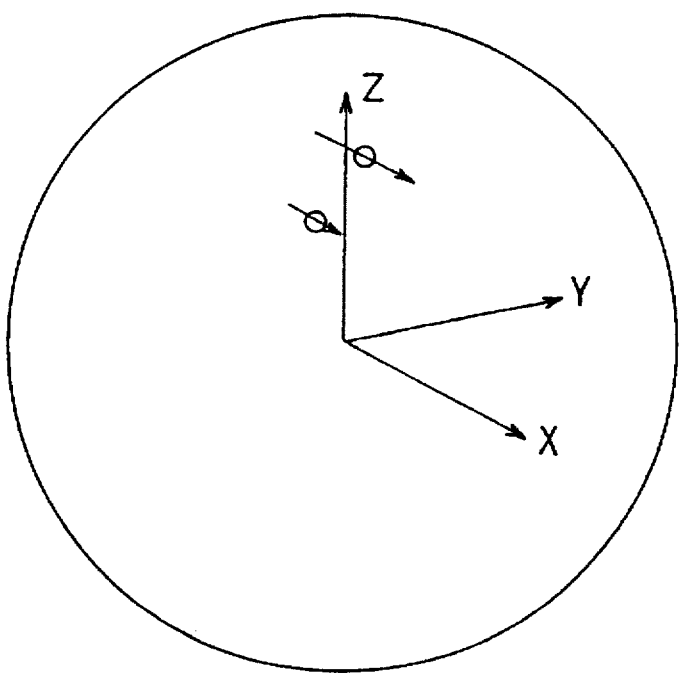
FIG. 32 is a view showing a reconstruction of current sources obtained in a simulation of the seventh embodiment.

FIG. 32 shows results of a simulation of the seventh embodiment which assumes that a current source (10, 0, 0) [nAm] is present in the position (0, 10, 69.0) [mm], a current source (10, 0, 0) [nAm] in the position (0, −10, 49.0) [mm], and 32 lattice points are set ,to magnetic fields determined by measuring these magnetic fields with 129 magnetic sensors (with a signal to noise ratio=20). It is seen that, according to this embodiment, the current sources are deduced accurately even if noise is mixed into the magnetic fields measured.

Eighth Embodiment

The technique described in the seventh embodiment is capable of excellent deduction where the current sources are assumed to be current dipoles. However, the current sources deduced tend to consolidate (or concentrate locally) since the penalty term is added to the particular criterion for an optimal current source (step S63 in FIG. 30). This results in the disadvantage that, where current sources are distributed over a certain range, such current sources are difficult to deduce correctly. In view of this disadvantage, this embodiment is intended to correctly deduce distributed current sources.

Figure 33:
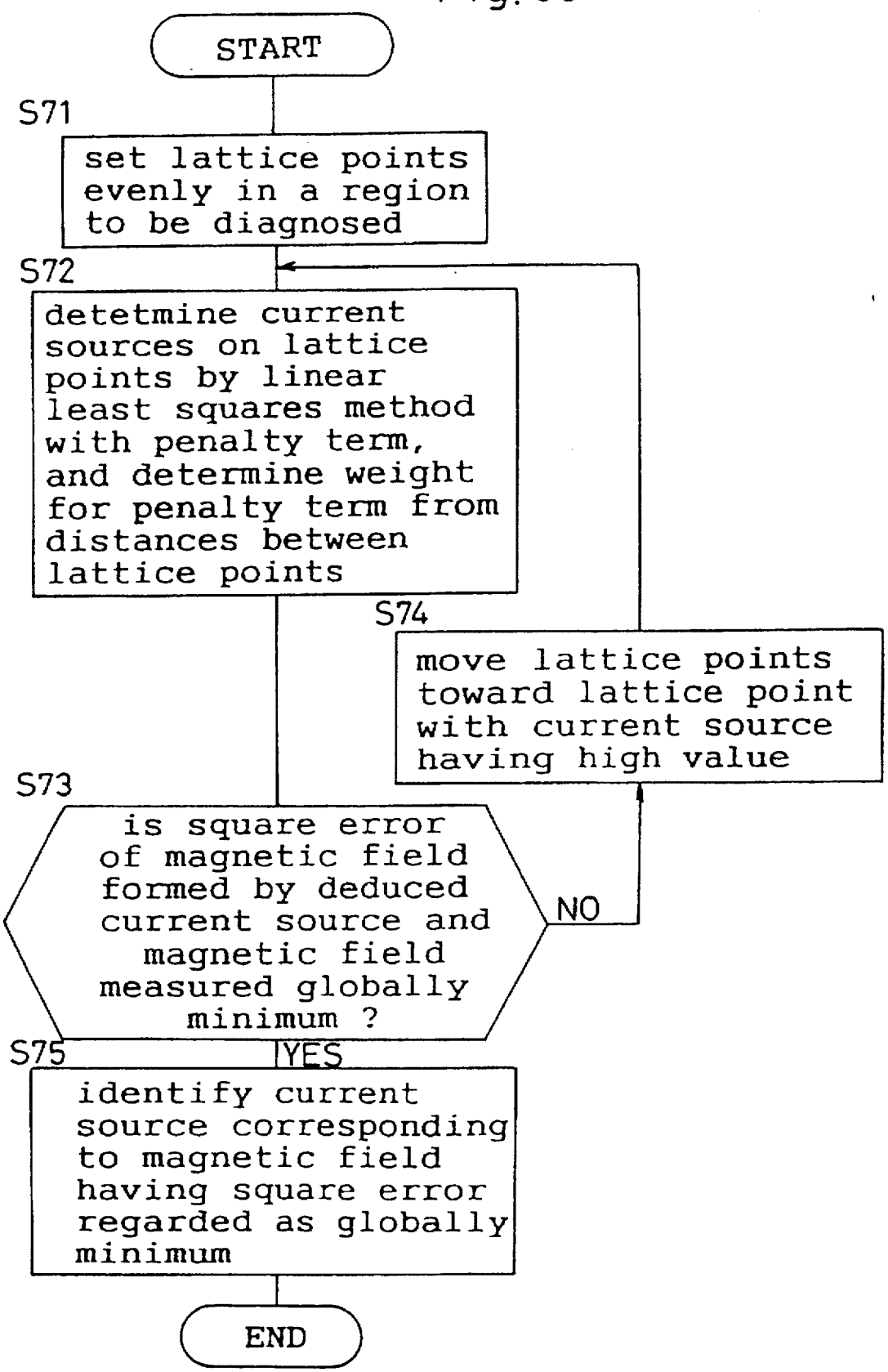
FIG. 33 is a flowchart of current source deduction processing in an eighth embodiment.

This embodiment will be described hereinafter with reference to the flowchart shown in FIG. 33.

At step S71, lattice points are set evenly in a region to be diagnosed, as in the seventh embodiment. Then, step S72 is executed to determine current sources [P] from magnetic fields [Bd] detected by the magnetic sensors S1–Sm, using the linear least squares method. At this time, as at step S62 in the seventh embodiment, this embodiment also adds the condition to minimize evaluation function f expressed by the sum of square error |[Bd]−[B]| between measured magnetic fields [Bd] and current sources [B] applied to the magnetic sensors S1–Sm by current sources [P] assumed for the respective lattice points, and the penalty term.

Here, weight λ of the penalty term in equation (11) is determined according to distances between lattice points. Specifically, a distance between each lattice point and the lattice point closest thereto is determined. Then, weight λ is determined using an average of the distances such that the smaller the average is, the smaller weight λ is. Consequently, weight λ increases when the lattice points are scattered, thereby increasing the influence of the penalty term in equation (11). In this way, variations in the deduced current sources due to noise components may be suppressed. On the other hand, weight λ decreases when the lattice points are locally concentrated, thereby diminishing the influence of the penalty term in equation (11). Thus, an undue concentration of the current sources may be avoided.

After current sources [P] are determined, step S73 is executed to check whether the square error between current sources [B] applied to the magnetic sensors S1–Sm by current sources [P] assumed and measured magnetic fields [Bd] is a global minimum or not. That is, since the penalty term is excluded from the particular criterion for optimal current sources, adoption of unnecessarily concentrated current sources as optimal current sources is avoided. If the square error is found not to be a global minimum, the operation proceeds to step S74 for moving the lattice points to the vicinity of the lattice point having the greatest current source as in the seventh embodiment. Then, the operation returns to step S72 for newly obtaining current sources [P] for the moved lattice points by the linear least squares method to which the penalty term is added as before. Then, step S73 is executed again to determine whether the square error is a global minimum or not. If the square error is found not to be a minimum, steps S72–S74 are repeated. If the square error is found to be a global minimum at step S67, step S75 is executed to regard current source [P] providing the globally minimum current source [B] as the true current source. This completes the processing sequence.

<simulation>

Figure 34:
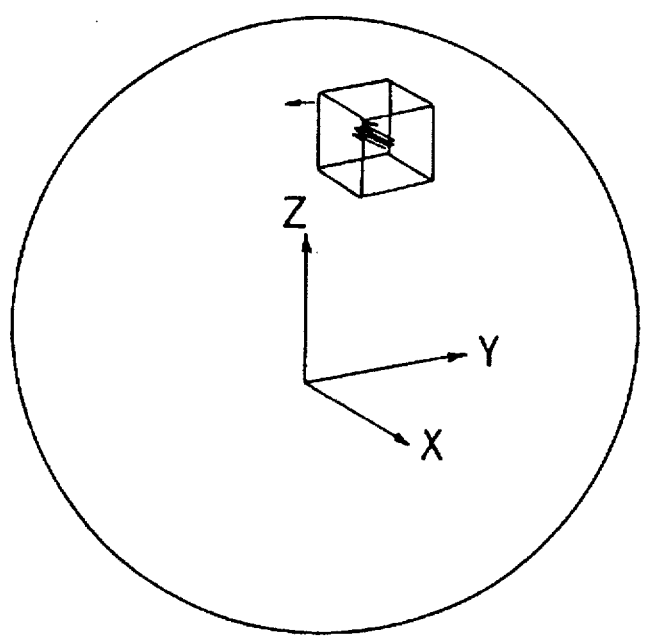
FIG. 34 is a view showing a reconstruction of current sources obtained from the seventh embodiment, for comparison purposes.
Figure 35:
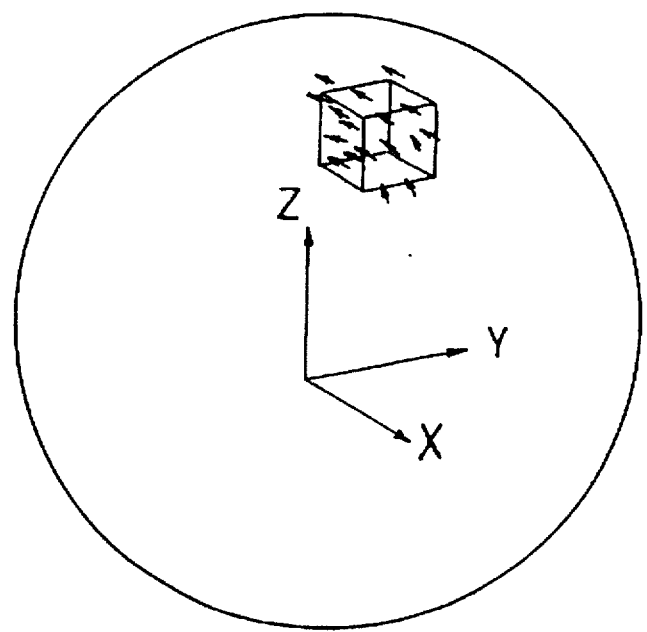
FIG. 35 is a view showing a reconstruction of current sources obtained in a simulation of the eighth embodiment.

Simulations were carried out to ascertain functions of the above technique visually. FIG. 34 shows results of a simulation of the foregoing seventh embodiment which assumes that current sources of 10 nA are uniformly distributed around a position (0, 20, 60) [mm] in a cube of 20 mm at each side. Based on the magnetic fields determined by measuring these magnetic fields in a uniform distribution with 129 magnetic sensors (with a signal to noise ratio=20), 32 lattice points are set. According to the technique of the seventh embodiment, the current sources deduced are excessively concentrated. FIG. 35 shows results of a simulation of the eighth embodiment in which a similar uniform distribution of current sources are deduced. It is seen that, according to the eighth embodiment, the current sources in the uniform distribution are deduced in a correct form.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method of deducing physical quantities including positions, sizes and orientations of bioelectric current sources, said method comprising:

a magnetic field measuring step for measuring minute magnetic fields formed by said bioelectric current sources in a region under examination of an examinee, with a plurality of magnetic sensors arranged adjacent said region under examination;

a lattice point setting step for setting a plurality of lattice points in said region under examination;

a current source computing step for deriving physical quantities of said current sources by solving a relational expression of unknown current sources at said lattice points and field data provided by said magnetic sensors, with a condition added thereto to minimize a norm of a vector having the current source at each of said lattice points;

a lattice point rearranging step for moving said lattice points toward a lattice point having a large current value among the current sources computed;

a checking step for checking whether a minimum distance among said lattice points having been moved is below a predetermined value;

a current source identifying step for repeating said current source computing step to said checking step for said lattice points having been moved, when said minimum distance exceeds said predetermined value, and regarding as a true current source the current source corresponding to a magnetic field occurring when said minimum distance is determined to be below said predetermined value at said checking step;

a likelihood computing step for deriving likelihood of current sources being present at said lattice points from said physical quantities of said current sources at said lattice points determined at said current source computing step; and a lattice point dividing step for dividing said lattice points into a plurality of groups based on the likelihood derived;

wherein said lattice point rearranging step is executed to move said lattice points toward a lattice point having the largest current value in each of said groups into which said lattice points have been divided at said lattice point dividing step, wherein said magnetic field measuring step is executed to measure simultaneously three orthogonal components of said minute magnetic fields formed by said bioelectric current sources in said region under examination, with said plurality of magnetic sensors arranged adjacent said region under examination;

wherein said current source computing step is executed to derive physical quantities of said current sources by solving a relational expression of unknown current sources at said lattice points and field data of said three orthogonal components provided by said magnetic sensors, with said condition added thereto to minimize a norm of a vector having the current source at each of said lattice points; and wherein said likelihood computing step is executed to derive likelihood of current sources being present at said lattice points from sizes (intensities) of said current sources at said lattice points determined at said current source computing step.

2. An apparatus for deducing physical quantities including positions, sizes and orientations of bioelectric current sources, said apparatus comprising:

a plurality of magnetic sensors arranged adjacent a region under examination of an examinee for measuring minute magnetic fields formed by said bioelectric current sources in said region under examination;

data converting means for converting field data measured by said magnetic sensors into digital data;

data collecting means for collecting and storing the field data converted into the digital data;

lattice point setting means for setting a plurality of lattice points in said region under examination;

current source computing means for deriving physical quantities of said current sources by solving a relational expression of unknown current sources at said lattice points and said field data stored in said data collecting means, with a condition added thereto to minimize a norm of a vector having the current source at each of said lattice points;

lattice point rearranging means for moving said lattice points toward a lattice point having a large current value among the current sources computed;

checking means for checking whether a minimum distance among said lattice points having been moved is below a predetermined valve;

current source identifying means for repeatedly causing said current source computing means, said lattice point rearranging means and said checking means to process said lattice points having been moved, when said minimum distance exceeds said predetermined value, and regarding as a true current source the current source corresponding to a magnetic field occurring when said minimum distance is determined to be below said predetermined value by said checking means;

display means for displaying said current source identified by said current source identifying means, in superposition on a sectional image of said region under examination;

likelihood computing means for deriving likelihood of current sources being present at said lattice points from said physical quantities of said current sources at said lattice points determined by said current source computing means; and lattice point dividing means for dividing said lattice points into a plurality of groups based on the likelihood derived;

wherein said lattice point rearranging means is operable to move said lattice points toward a lattice point having the largest current value in each of said groups into which said lattice points have been divided by said lattice point dividing means;

wherein each of said magnetic sensors includes three pickup coils having detection sensitivity in three orthogonal directions for simultaneously detecting three orthogonal components of said minute magnetic fields formed by said bioelectric current sources in said region under examination;

wherein said current source computing means is operable to derive physical quantities of said current sources by solving a relational expression of unknown current sources at said lattice points and field data of said three orthogonal components stored in said data collecting means, with said condition added thereto to minimize a norm of a vector having the current source at each of said lattice points; and wherein said likelihood computing means is operable to derive likelihood of current sources being present at said lattice points from sizes (intensities) of said current sources at said lattice points determined by said current source computing means.

* * * * *